United States Patent
Yang et al.

(10) Patent No.: US 10,654,860 B2
(45) Date of Patent: May 19, 2020

(54) TRICYCLIC RHO KINASE INHIBITORS

(71) Applicant: BRISTOL-MYERS SQUIBB COMPANY, Princeton, NJ (US)

(72) Inventors: Wu Yang, Princeton Junction, NJ (US); Peter W. Glunz, Yardley, PA (US); Rajeev S. Bhide, Princeton Junction, NJ (US); Kamalraj Thiyagarajan, Vellore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/461,029

(22) PCT Filed: Nov. 29, 2017

(86) PCT No.: PCT/US2017/063554
§ 371 (c)(1),
(2) Date: May 15, 2019

(87) PCT Pub. No.: WO2018/102325
PCT Pub. Date: Jun. 7, 2018

(65) Prior Publication Data
US 2019/0276466 A1 Sep. 12, 2019

Related U.S. Application Data

(60) Provisional application No. 62/427,875, filed on Nov. 30, 2016.

(51) Int. Cl.
| | | |
|---|---|---|
| *C07D 487/10* | (2006.01) | |
| *C07D 403/10* | (2006.01) | |
| *C07D 471/04* | (2006.01) | |
| *C07D 491/052* | (2006.01) | |
| *C07D 491/147* | (2006.01) | |
| *C07D 231/54* | (2006.01) | |
| *C07D 487/04* | (2006.01) | |
| *C07D 403/04* | (2006.01) | |
| *A61K 31/436* | (2006.01) | |

(52) U.S. Cl.
CPC ......... *C07D 487/10* (2013.01); *C07D 231/54* (2013.01); *C07D 403/04* (2013.01); *C07D 403/10* (2013.01); *C07D 471/04* (2013.01); *C07D 487/04* (2013.01); *C07D 491/052* (2013.01); *C07D 491/147* (2013.01)

(58) Field of Classification Search
None
See application file for complete search history.

(56) References Cited

U.S. PATENT DOCUMENTS

2014/0243338 A1   8/2014   Quan

FOREIGN PATENT DOCUMENTS

| WO | WO2014113620 A2 | 7/2014 |
|---|---|---|
| WO | WO2014134391 A1 | 9/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2017205709 A1 | 11/2017 |
| WO | WO2018009622 A1 | 1/2018 |
| WO | WO2018009625 A1 | 1/2018 |
| WO | WO2018009627 A1 | 1/2018 |
| WO | WO2018102325 A1 | 6/2018 |
| WO | WO2019014300 A1 | 1/2019 |
| WO | WO2019014303 A1 | 1/2019 |
| WO | WO2019014304 A1 | 1/2019 |
| WO | WO2019014308 A1 | 1/2019 |
| WO | WO2019089868 A1 | 5/2019 |

OTHER PUBLICATIONS

Mei et al., "Discovery of potent and selective urea-based ROCK inhibitors: Exploring the inhibitor's potency and ROCK2/PKA selectivity by 3D-QSAR, molecular docking and molecular dynamics simulations", Bioorganic & Medicinal Chemistry, vol. 23, pp. 2505-2517 (2015).

*Primary Examiner* — Zinna Northington Davis
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

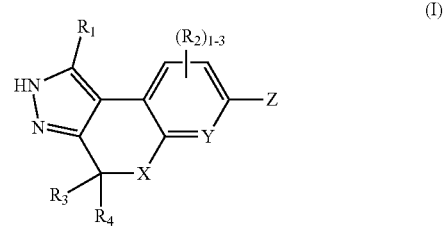

15 Claims, No Drawings

TRICYCLIC RHO KINASE INHIBITORS

CROSS REFERENCE TO RELATED APPLICATIONS

This application is a 371 application of PCT/US2017/063554 filed Nov. 29, 2017 which is entitled to priority pursuant to 35 U.S.C. § 119(e) to U.S. provisional patent application No. 62/427,875, filed on Nov. 30, 2016, which is incorporated herein in its entirety.

FIELD OF THE INVENTION

The present invention relates to novel tricyclic compounds, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms. ROCK1 and ROCK2 (Ishizaki, T. et al., *EMBO J.* 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.,* 4:446-456 (2003)). It is also directly involved in regulating smooth muscle contraction (Somlyo, A. P., *Nature,* 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension,* 35:313-318 (2000)), urotensin II (Sauzeau, V. et al., *Circ. Res.,* 88:1102-1104 (2001)), endothelin-1 (Tangkijvanich, P. et al., *Hepatology,* 33:74-80 (2001)), serotonin (Shimokawa, H., *Jpn. Circ. J.,* 64:1-12 (2000)), norepinephrine (Martinez, M. C. et al., *Am. J. Physiol.,* 279:H1228-H1238 (2000)) and platelet-derived growth factor (PDGF) (Kishi, H. et al., *J. Biochem.,* 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.,* 241:1033-1040 (1987)) or Y-27632 (Uehata, M. et al., *Nature,* 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.,* 15:1062-1064 (2001)). The ROCK inhibitor Y-27632 (Uehata, M. et al., *Nature, ibid.*) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.,* 278:H1744-H1750 (2000)). In a similar model, ROCK inhibitor Y-27632 also inhibited neointimal formation in rats (Sawada, N. et al., *Circulation,* 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.,* 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke,* 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.,* 55:757-767 (2002)).

Other animal or clinical studies have implicated ROCK in additional diseases including coronary vasospasm (Shimokawa, H. et al., *Cardiovasc. Res.,* 43:1029-1039 (1999)), cerebral vasospasm (Sato, M. et al., *Circ. Res.,* 87:195-200 (2000)), ischemia/reperfusion injury (Yada, T. et al., *J. Am. Coll. Cardiol.,* 45:599-607 (2005)), pulmonary hypertension (Fukumnoto, Y. et al., *Heart,* 91:391-392 (2005)), angina (Shimokawa, H. et al., *J. Cardiovasc. Pharmacol.,* 39:319-327 (2002)), renal disease (Satoh, S. et al., *Eur. J. Pharmacol.,* 455:169-174 (2002)) and erectile dysfunction (Gonzalez-Cadavid, N. F. et al., *Enocrine,* 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.,* 278:13578-13584 (2003)). It has also been reported that small molecule inhibitors of Rho Kinase are capable of inhibiting MCP-1 mediated chemotaxis in vitro (Iijima, H., *Bioorg. Med Chem.,* 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vase. Biol.,* 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.,* 18:67-74 (2005)), cancer (Rattan, R. et al., *J. Neurosci. Res.,* 83:243-255 (2006); Lepley, D. et al., *Cancer Res.,* 65:3788-3795 (2005)), fibrotic diseases (Jiang, C. et al., *Int. J. Mol. Sci.,* 13:8293-8307 (2012); Zhou, L. et al., *Am. J. Nephrol.,*

34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel tricyclic compounds including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

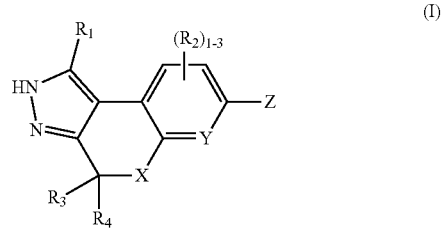

or stereoisomers, enantiomers, diastereoisomers, tautomers, pharmaceutically acceptable salts, solvates, or prodrugs thereof, wherein X is independently selected from —CR$_3$R$_4$—, —O—, and NR$_{5a}$;

Y is independently selected from —CR$_2$ and N;

Z is independently selected from —NR$_5$C(O)NR$_5$(CR$_6$R$_7$)$_q$—R$_8$, —NR$_5$C(O)(CR$_6$R$_7$)$_q$—R$_8$, C(O)NR$_5$(CR$_6$R$_7$)$_q$—R$_8$,

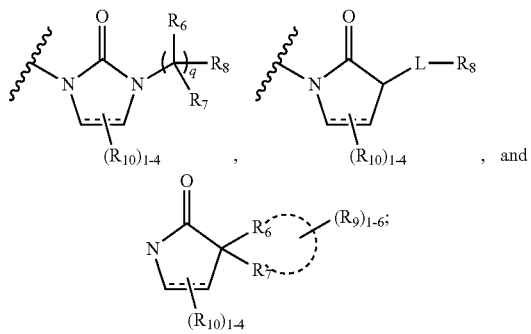

--- is an optional bond;

L is independently selected from —(CR$_6$R$_7$)$_q$—, —NR$_{5a}$(CR$_6$R$_7$)$_q$—, and —O(CR$_6$R$_7$)$_q$—;

R$_1$ is independently selected from H, F, Cl, Br, CN, NR$_a$R$_a$, —OC$_{1-4}$ alkyl substituted with 0-3 Re, C$_{1-4}$ alkyl substituted with 0-3 R$_e$, and —(CH$_2$)$_r$OR$_b$;

R$_2$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, —(CH$_2$)$_r$OR$_b$;

R$_3$ and R$_4$ are independently selected from H and C$_{1-4}$ alkyl substituted with 0-3 R$_e$;

R$_5$ is independently selected from H and C$_{1-4}$ alkyl;

R$_{5a}$ is independently selected from H and C$_{1-4}$ alkyl;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O) NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

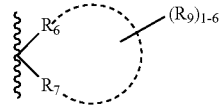

is independently selected from carbocyclyl and heterocyclyl;

R$_8$ is selected from C$_{3-10}$carbocyclyl and heterocyclyl, each substituted with 1-5 R$_9$;

R$_9$ is independently selected from H, F, Cl, Br, C$_{1-4}$alkyl substituted with 0-5 R$_e$, C$_{2-4}$alkenyl substituted with 0-5 R$_e$, C$_{2-4}$alkynyl substituted with 0-5 R$_e$, =O, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, (CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O) NR$_a$R$_a$, —(CHR$_d$)$_r$C(=O)OR$_b$, —(CHR$_d$)$_r$C(=O)R$_b$, —(CHR$_d$)$_r$ OC(=O)R$_b$ —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_{10}$ is independently selected from H, =O, C$_{1-4}$alkyl substituted with 0-4 R$_e$, —(CH$_2$)$_r$OR$_b$, C(=O)R$_b$, and —C(=O)OR$_b$;

R$_a$, at each occurrence, is independently selected from H, C$_{1-6}$ alkyl substituted with 0-5 R$_e$, C$_{2-6}$alkenyl substituted with 0-5 R$_e$, C$_{2-6}$alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$.

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl (optionally substituted with F, Cl, and Br, OH), C$_{2-6}$ alkenyl, C$_{2-6}$ alkynyl, —(CH$_2$)$_r$—C$_{3-10}$ carbocyclyl, —(CH$_2$)$_r$-heterocyclyl, F, Cl, Br, CN, NO$_2$, =O, CO$_2$H, CO$_2$C$_{1-6}$ alkyl, —(CH$_2$)$_r$OC$_{1-5}$ alkyl, —(CH$_2$)$_r$OH, —(CH$_2$)$_r$NR$_f$R$_f$, —(CH$_2$)$_r$NR$_f$R$_f$C(=O) C$_{1-4}$alkyl, —C(=O)NR$_f$R$_f$, —C(=O)R$_f$, S(O)$_p$NR$_f$R$_f$, —NR$_f$R$_f$S(O)$_p$C$_{1-4}$alkyl, and S(O)$_p$C$_{1-4}$alkyl;

R$_f$, at each occurrence, is independently selected from H, F, Cl, Br, C$_{1-5}$alkyl, C$_{3-6}$ cycloalkyl; or R$_f$ and R$_f$ together with the nitrogen atom to which they are both attached form a heterocyclic ring;

p, at each occurrence, is independently selected from zero, 1, and 2;

q, at each occurrence, is independently selected from zero, 1, 2, and 3; and r, at each occurrence, is independently selected from zero, 1, 2, 3, and 4.

In another aspect, the present invention provides compounds of Formula (II):

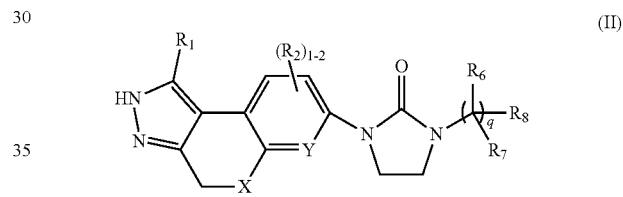

(II)

or stereoisomers, enantiomers, diastereoisomers, tautomers, pharmaceutically acceptable salts, solvates, or prodrugs thereof, wherein X is independently selected from —CH$_2$—, and —O—;

Y is independently selected from —CR$_2$ and N;

R$_1$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, and —(CH$_2$)$_r$OR$_b$;

R$_2$ is independently selected from H, F, Cl, Br, CN, NR$_a$R$_a$, —OC$_{1-4}$ alkyl substituted with 0-3 R$_e$, C$_{1-4}$ alkyl substituted with 0-3 R$_e$, and —(CH$_2$)$_r$OR$_b$;

R$_6$ and R$_7$ are independently selected from H and C$_{1-4}$alkyl substituted with 0-4 R$_e$;

R$_8$ is selected from phenyl, C$_{3-6}$ cycloalkyl and heterocyclyl, each substituted with 1-5 R$_9$;

R$_9$ is independently selected from H, F, Cl, C$_{1-4}$alkyl substituted with 0-5 R$_e$, —C(=O)NR$_a$R$_a$, —NR$_a$S(O)$_p$C$_{1-4}$ alkyl, —OR$_b$, and —CN;

R$_a$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_b$, at each occurrence, is independently selected from H and C$_{1-6}$ alkyl substituted with 0-5 R$_e$;

R$_e$, at each occurrence, is independently selected from C$_{1-6}$ alkyl (optionally substituted with F, Cl, and Br, OH), F, Cl, Br, CN, NO$_2$, —(CH$_2$)$_r$OC$_{1-5}$ alkyl, —(CH$_2$)$_r$OH;

p, at each occurrence, is independently selected from zero, 1, and 2;

q, at each occurrence, is independently selected from zero, 1, 2, and 3; and r, at each occurrence, is independently selected from zero, 1, 2, 3, and 4.

In another aspect, the present invention provides compounds of Formula (III):

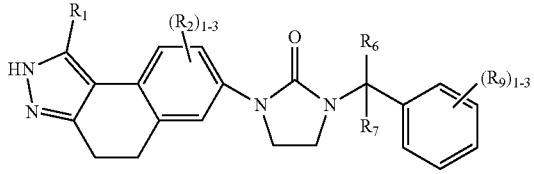

(III)

or stereoisomers, tautomers, pharmaceutically acceptable salts, solvates, or prodrugs thereof, wherein $R_1$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_2$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_6$ and $R_7$ are independently selected from H and Me:

$R_9$ is independently selected from H, F, Cl, $C_{1-4}$ alkyl substituted with 0-5 $R_e$, and $-OC_{1-4}$ alkyl;

$R_a$, at each occurrence, is independently selected from H, $C_{1-6}$ alkyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, $-(CH_2)OC_{1-5}$ alkyl, $-(CH_2)_rOH$; and r, at each occurrence, is independently selected from zero, 1, 2, 3, and 4.

In another aspect, the present invention provides compounds of Formula (IV):

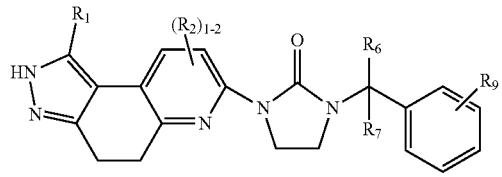

(IV)

or stereoisomers, tautomers, pharmaceutically acceptable salts, solvates, or prodrugs thereof, wherein $R_1$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_2$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_6$ and $R_7$ are independently selected from H and Me;

$R_9$ is independently selected from H, F, Cl, $C_{1-4}$ alkyl substituted with 0-5 $R_e$, and $-OC_{1-4}$ alkyl;

$R_a$, at each occurrence, is independently selected from H, $C_{1-6}$ alkyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, $-(CH_2)_rOC_{1-5}$ alkyl, $-(CH_2)_rOH$; and r, at each occurrence, is independently selected from zero, 1, 2, 3, and 4.

In another aspect, the present invention provides compounds of Formula (V):

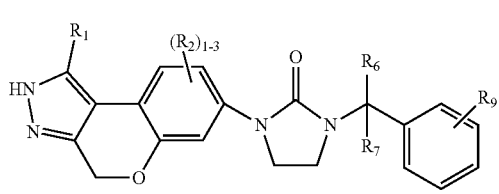

(V)

or stereoisomers, tautomers, pharmaceutically acceptable salts, solvates, or prodrugs thereof, wherein $R_1$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_2$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_6$ and $R_7$ are independently selected from H and Me;

$R_9$ is independently selected from H, F, Cl, $C_{1-4}$ alkyl substituted with 0-5 $R_e$, and $-OC_{1-4}$ alkyl:

$R_a$, at each occurrence, is independently selected from H, $C_{1-6}$ alkyl substituted with 0-5 $R_e$, $-(CH_2)_r-C_{3-10}$ carbocyclyl substituted with 0-5 $R_e$, and $-(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, $-(CH_2)_rOC_{1-5}$ alkyl, $-(CH_2)_rOH$; and r, at each occurrence, is independently selected from zero, 1, 2, 3, and 4.

In another aspect, the present invention provides compounds of Formula (VI):

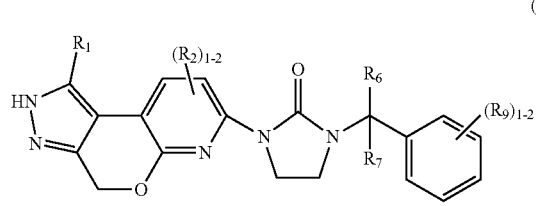

(VI)

or stereoisomers, tautomers, pharmaceutically acceptable salts, solvates, or prodrugs thereof, wherein $R_1$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_2$ is independently selected from H, F, Cl, Br, CN, $NR_aR_a$, $-OC_{1-4}$ alkyl substituted with 0-3 $R_e$, $C_{1-4}$ alkyl substituted with 0-3 $R_e$, and $-(CH_2)_rOR_b$;

$R_6$ and $R_7$ are independently selected from H and Me;

$R_9$ is independently selected from H, F, Cl, $C_{1-4}$alkyl substituted with 0-5 $R_e$, and —$OC_{1-4}$alkyl;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and r, at each occurrence, is independently selected from zero, 1, 2, 3, and 4.

In another aspect, the present invention provides compounds of Formula (VII):

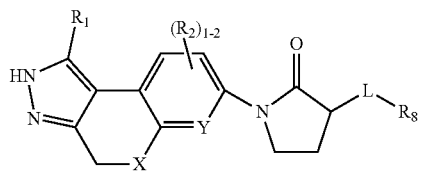

(VII)

or stereoisomers, enantiomers, diastereoisomers, tautomers, pharmaceutically acceptable salts, solvates, or prodrugs thereof, wherein X is independently selected from —$CH_2$—, and —O—;

Y is independently selected from —$CR_2$ and N;

L is independently selected from —$CR_6R_7$—, —$NR_{5a}$—, and —O—;

$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_6$ and $R_7$ are independently selected from H and $C_{1-4}$alkyl substituted;

$R_8$ is selected from phenyl, $C_{3-6}$ cycloalkyl and heterocyclyl, each substituted with 1-5 $R_9$;

$R_9$ is independently selected from H, F, Cl, $C_{1-4}$alkyl substituted with 0-5 $R_e$, —$OR_b$, and heteroaryl;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$;

p, at each occurrence, is independently selected from zero, 1, and 2; and r, at each occurrence, is independently selected from zero, 1, 2, 3, and 4.

In another aspect, the present invention provides compounds of Formula (VIII):

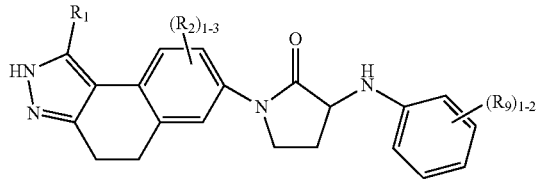

(VIII)

or stereoisomers, enantiomers, diastereoisomers, tautomers, pharmaceutically acceptable salts, solvates, or prodrugs thereof, wherein $R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_9$ is independently selected from H, F, Cl, CN, $C_{1-4}$alkyl substituted with 0-5 $R_e$, and —$OC_{1-4}$alkyl;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and r, at each occurrence, is independently selected from zero, 1, 2, 3, and 4.

In another aspect, the present invention provides compounds of Formula (IX):

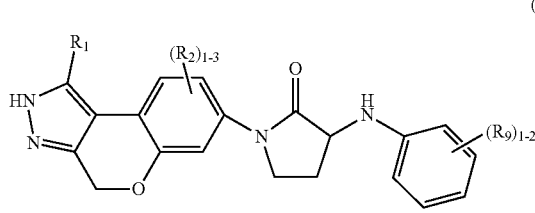

(IX)

or stereoisomers, enantiomers, diastereoisomers, tautomers, pharmaceutically acceptable salts, solvates, or prodrugs thereof, wherein $R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_9$ is independently selected from H, F, Cl, CN, $C_{1-4}$alkyl substituted with 0-5 $R_e$, and —$OC_{1-4}$alkyl;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and r, at each occurrence, is independently selected from zero, 1, 2, 3, and 4.

In another aspect, the present invention provides compounds of Formula (X):

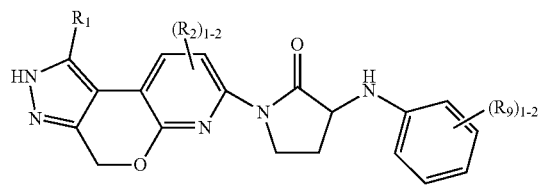

(X)

or stereoisomers, enantiomers, diastereoisomers, tautomers, pharmaceutically acceptable salts, solvates, or prodrugs thereof, wherein $R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_9$ is independently selected from H, F, Cl, CN, $C_{1-4}$alkyl substituted with 0-5 $R_e$, and —$OC_{1-4}$alkyl;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and r, at each occurrence, is independently selected from zero, 1, 2, 3, and 4.

In another aspect, the present invention provides compounds of Formula (XI):

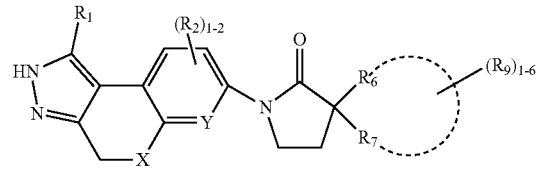

(XI)

or stereoisomers, enantiomers, diastereoisomers, tautomers, pharmaceutically acceptable salts, solvates, or prodrugs thereof, wherein

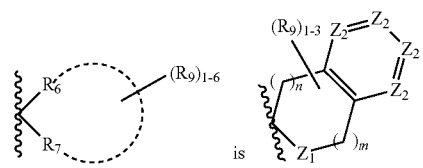

is

X is independently selected from —$CH_2$—, and —O—;
Y is independently selected from —$CR_2$ and N;

$Z_1$ is independently selected from $CR_9R_9$, O, NH, and $NC_{1-4}$alkyl;

$Z_2$ is independently selected from $CR_9$ and N; provided no more than three of $Z_2$ are N;

$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_9$ is independently selected from H, F, Cl, and $C_{1-4}$ alkyl substituted with 0-5 $R_e$;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$;

m is independently selected from 0 and 1;
n is independently selected from 1 and 2; and
r, at each occurrence, is independently selected from zero, 1, 2, 3, and 4.

In another aspect, the present invention provides compounds of Formula (XII):

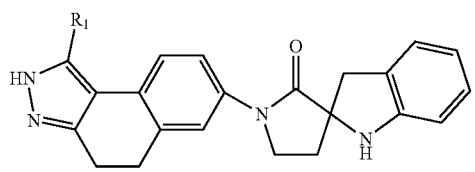

(XII)

or stereoisomers, enantiomers, diastereoisomers, tautomers, pharmaceutically acceptable salts, solvates, or prodrugs thereof, wherein R is independently selected from H and $C_{1-4}$ alkyl.

In another aspect, the present invention provides compounds of Formula (XIII):

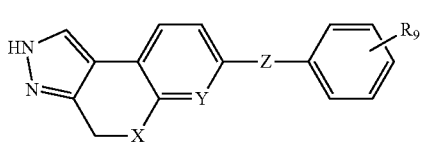

(XIII)

or stereoisomers, enantiomers, diastereoisomers, tautomers, pharmaceutically acceptable salts, solvates, or prodrugs thereof, wherein
or a stereoisomer, tautomer, pharmaceutically acceptable salt thereof, wherein X is independently selected from —$CH_2$—, and —O—;
Y is independently selected from —$CR_2$ and N;
Z is independently selected from —$NR_5C(O)NR_5(CR_6R_7)_q$—, —$NR_5C(O)CR_6R_7$-L-, and —$C(O)NR_5(CR_6R_7)_q$—;
L is independently selected from —$(CR_6R_7)_q$—, and —$NR_{5a}(CR_6R_7)_q$—;
$R_6$ and $R_7$ are independently selected from H, $C_{1-4}$alkyl, and $NH_2$;

$R_9$ is independently selected from H, F, Cl, $C_{1-4}$alkyl, and —$OC_{1-4}$alkyl; and q, at each occurrence, is independently selected from zero, 1, and 2.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments.

In another aspect, the present invention provides a compound selected from any subset list of compounds exemplified in the present application.

In another embodiment, the compounds of the present invention have ROCK $IC_{50}$ values≤10 μM.

In another embodiment, the compounds of the present invention have ROCK $IC_{50}$ values≤1 μM.

In another embodiment, the compounds of the present invention have ROCK $IC_{50}$ values≤0.5 μM.

In another embodiment, the compounds of the present invention have ROCK $IC_{50}$ values≤0.1 μM.

In another embodiment, the compounds of the present invention have ROCK $IC_{50}$ values≤0.05 μM.

In another embodiment, the compounds of the present invention have ROCK $IC_{50}$ values≤0.01 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed chemical Dictionary,* 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazol, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocyclyl" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxy carbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
AlCl$_3$ aluminum chloride
AIBN Azobisisobutyronitrile
BBr$_3$ boron tribromide
BOP reagent benzotriazol-1-yloxytris(dimethylamino)phosphonium hexafluorophosphate
CBz carbobenzyloxy
DCM or CH$_2$Cl$_2$ dichloromethane
CH$_3$CN or ACN acetonitrile
CDCl$_3$ deutero-chloroform
CHCl$_3$ chloroform mCPBA or m-CPBA meta-chloroperbenzoic acid
Cs$_2$CO$_3$ cesium carbonate
Cu(OAc)$_2$ copper (II) acetate
DBU 1,8-diazabicyclo[5.4.0]undec-7-ene
DCE 1,2 dichloroethane
DEA diethylamine
DIEA, DIPEA or diisopropylethylamine
Hunig's base
DMAP 4-dimethylaminopyridine
DME 1,2-dimethoxy ethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylarinopropyl)-N'-ethylcarbodiimide
EDCI N-(3-dimthylaminopropyl)-N'-ethyl carbodiimide hydrochloride
Et$_3$N or TEA triethylamine
EtOAc ethyl acetate
Et$_2$O diethyl ether
EtOH ethanol
HCl hydrochloric acid
HATU O-(7-azabenzotriazol-1-yl)-N,N,N',N'-tetramethyl-uronium hexafluorophosphate
Hex hexane
HOBt or HOBT 1-hydroxybenzotriazole
K$_2$CO$_3$ potassium carbonate
KOAc potassium acetate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4$CO$_2$H ammonium formate
Pd$_2$(dba)$_3$ tris(dibenzylideneacetone)dipalladium(O)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
PG protecting group
POCl$_3$ phosphorus oxychloride
PPTS pyridinium p-toluenesulfonate
i-PrOH or IPA isopropanol
RT room temperature
SEM-Cl 2-(trimethysilyl)ethoxymethyl chloride
SiO$_2$ silica oxide
TFA trifluoroacetic acid
THF tetrahydrofuran
T3P propane phosphonic acid anhydride
pTsOH p-toluenesulfonic acid The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL, assay containing 20 mM HEPES, pH 7.5, 20 mM MgCl$_2$, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

Representative Examples were tested in the ROCK2 assay described above and found having ROCK2 inhibitory activity. Their ROCK2 inhibitory activity (IC$_{50}$ values) of ≤2 μM (2000 nM) was observed and shown in Table A below. The ranges of the ROCK2 IC$_{50}$ values are as follows: ROCK2 IC$_{50}$: ++++(<10 nM)+++(10-100 nM)++(100-500 nM)+ (500-2000 nM)

TABLE A

| Example No. | ROCK2 IC$_{50}$ |
|---|---|
| 1 | ++++ |
| 2 | ++++ |
| 3 | ++++ |
| 4 | ++++ |
| 5 | +++ |
| 6 | ++++ |
| 7 | ++++ |
| 8 | ++++ |
| 9 | ++++ |
| 10 | ++++ |
| 11 | +++ |
| 12 | +++ |
| 13 | ++++ |
| 14 | ++++ |
| 15 | ++++ |
| 16 | +++ |
| 17 | +++ |
| 18 | +++ |
| 19 | +++ |
| 20 | +++ |
| 21 | +++ |
| 22 | +++ |
| 23 | +++ |
| 24 | ++ |
| 25 | ++ |
| 26 | ++ |
| 27 | ++ |
| 28 | ++ |
| 29 | ++ |
| 30 | ++ |
| 31 | + |
| 32 | + |
| 33 | + |
| 34 | + |
| 35 | + |

V. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples sections set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

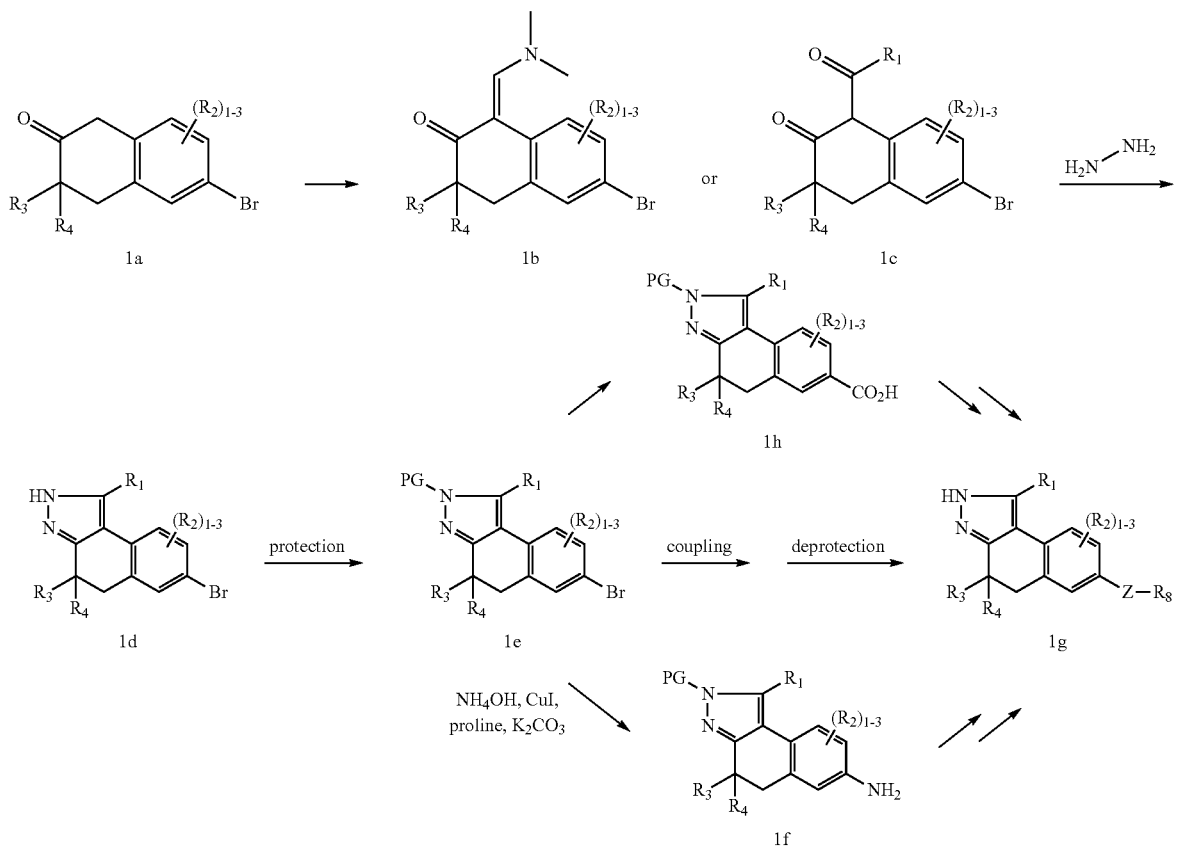

Scheme 1.

Scheme 1 shows the synthesis of generic compounds 1g. Bicyclic bromoketones 1a can be converted to 1,3-diketones 1c or 1,3-ketoaldehyde equivalent 1b, which upon treatment with hydrazine, provides fused tricyclic intermediates 1d. The pyrazole of 1d is protected either by Boc or preferably SEM group to form 1e as mixtures of regio-isomers. 1e can undergo N-arylation directly via palladium mediated coupling, which upon further functionalization and deprotection to provide compounds 1g. Alternatively, 1e can be converted to anilines 1f, which undergo direct amide coupling or reductive amination, followed by further functionalization and deprotection to afford the compounds 1g. Additionally, 1e can also be converted to carboxylic acid 1h via palladium mediated carbonylation or metal-halogen exchange followed by quenching with $CO_2$. Coupling of 1h with amines or anilines followed by deprotection affords compounds 1g.

intermediates 2d can be obtained by applying the same sequence as described in scheme 1 for the synthesis of intermediates 1d. m-CPBA oxidation of 2d, followed by $POCl_3$ treatment provides compounds 2e. 2e can be converted to 2f either through palladium mediated coupling, followed by deprotection, or via direct replacement of Cl with amines or anilines, followed by deprotection.

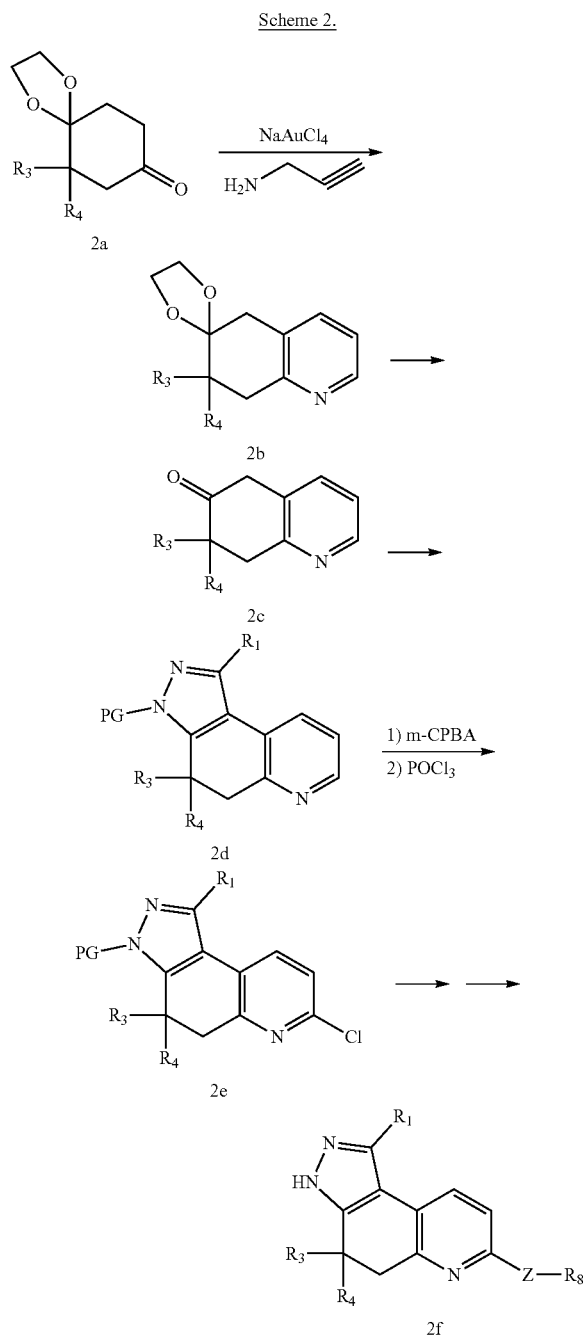

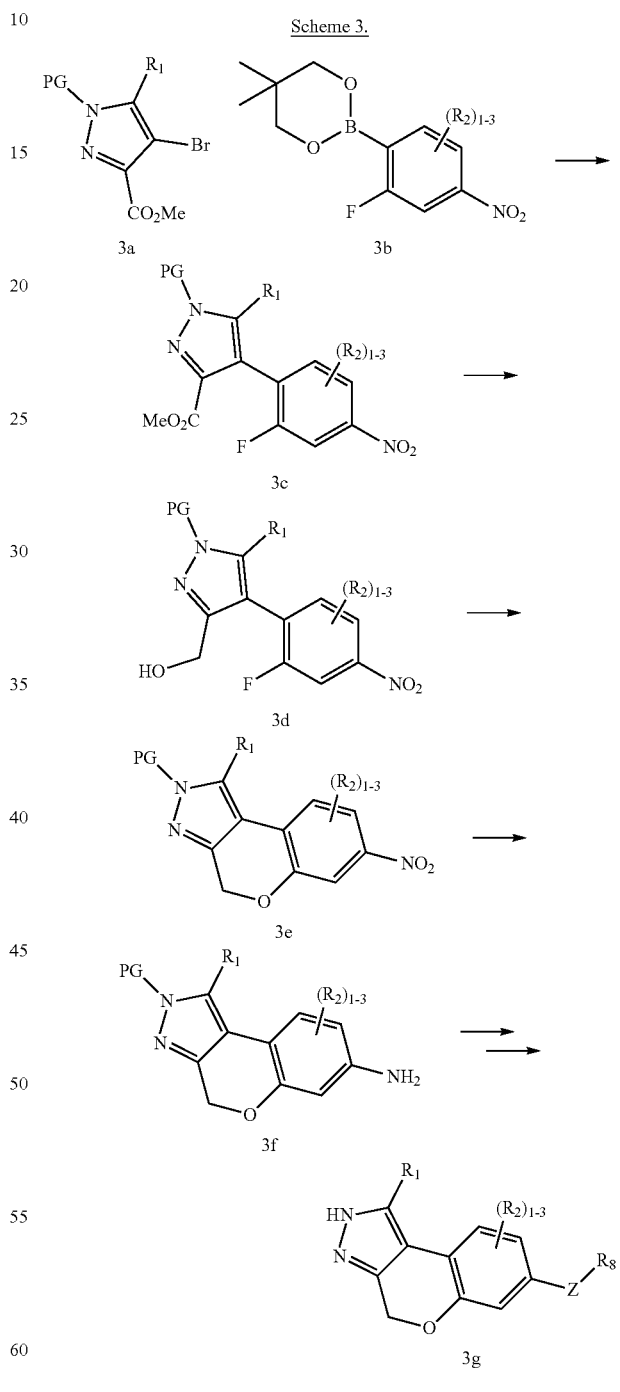

Scheme 2 shows the synthesis of generic fused tricyclic compounds 2f. Gold-mediated condensation of ketones 2a with propargyl amine provides bicyclic pyridine compounds 2b. Deprotection of 2b affords ketone 2c. The fused tricyclic Scheme 3 outlines the synthesis of generic fused tricyclic compounds 3g. Suzuki coupling of protected pyrazole bromides 3a with fluoro-, nitro-substituted phenyl boronates 3b provides compounds 3c. Reduction of methyl ester 3c to primary alcohol 3d, followed by cyclization affords compounds 3e. Reduction of the NO₂ group in 3e gives anilines 3f, which are further functionalized and deprotected to provide compounds 3g. Alternatively, the sequence of preparing 3d can be changed slightly by first reducing the methyl ester of 3a to its alcohol followed by Suzuki coupling to 3b.

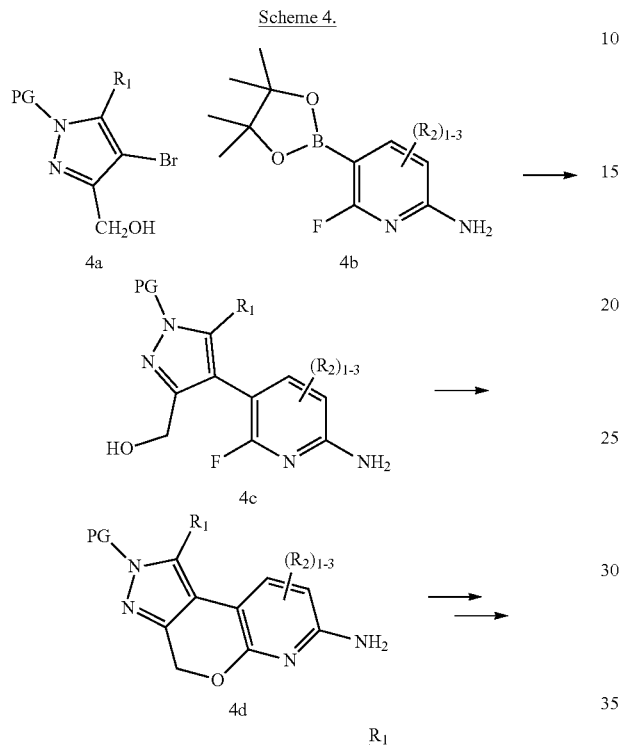

Scheme 4 shows the synthesis of generic fused tricyclic compounds 4e, which are prepared in a similar fashion as compounds 3g in scheme 3. Suzuki coupling of protected pyrazole bromides 4a with boronate of aminopyridines 4b affords compounds 4c. Cyclization of 4c provides 4d, which upon further functionalization and deprotection gives the final compounds 4e.

Purification of intermediates and final products was carried out via either normal or reverse phase chromatography. Normal phase chromatography was carried out using prepacked SiO₂ cartridges eluting with either gradients of hexanes and EtOAc or DCM and MeOH unless otherwise indicated. Reverse phase preparative HPLC was carried out using C18 columns eluting with gradients of Solvent A (90% H₂O, 10% MeOH, 0.1% TFA) and Solvent B (10% H₂O, 90% MeOH, 0.1% TFA, UV 220 nm) or with gradients of Solvent A (90% H₂O, 10% ACN, 0.1% TFA) and Solvent B (10% H₂O, 90% ACN, 0.1% TFA, UV 220 nm) or with gradients of Solvent A (98% H₂O, 2% ACN, 0.05% TFA) and Solvent B (98% ACN, 2% H₂O, 0.05% TFA, UV 220 nm) (or) Sunfire Prep C18 OBD 5u 30×100 mm, 25 min gradient from 0-100% B. A=H₂O/ACN/TFA 90:10:0.1. B=ACN/H₂O/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate: Gradient: 25-65% B over 20 minutes, then a 5-minute hold at 100% B; Flow: 20 mL/min.

Unless otherwise stated, analysis of final products was carried out by reverse phase analytical HPLC.

Method A: Waters Acquity UPLC BEH C18 (1.7 μm particle size, 2.1×50 mm); Solvent A: 5:95 acetonitrile:water with 10 mM ammonium acetate; Solvent B: 95:5 acetonitrile:water with 10 mM ammonium acetate; Temperature: 50 OC; Gradient: 0-100% B over 3 minutes, then hold at 100% B for 0.75-minute; Flow: 1.11 mL/min.

Method B: Waters Acquity UPLC BEH C18 (1.7 μm particle size, 2.1×50 mm); Solvent A: 5:95 acetonitrile:water with 0.1% TFA; Solvent B: 95:5 acetonitrile:water with 0.1% TFA; Temperature: 50° C.; Gradient: 0-100% B over 3 min, then hold at 100% B for 0.75 min; Flow: 1.11 mL/min.

Method C: Sunfire C18 column (3.5 μm particle size, 3.0×150 mum). Solvent A: 5:95 acetonitrile:water with 0.05% TFA; Solvent B: 95:5 acetonitrile:water with 0.05% TFA); Gradient elution from 10-100% Solvent B over 10 ruin, then hold at 100% B for 5 min; Flow: 1.0 mL/min.

Method D: XBridge Phenyl column (3.5 μm particle size, 3.0×150 mm). Solvent A: 5:95 acetonitrile:water with 0.05% TFA; Solvent B: 95:5 acetonitrile:water with 0.05% TFA); Gradient elution from 10-100% Solvent B over 10 min then hold at 100% B for 5 min; Flow: 1.0 mL/min.

Intermediate 1. 2-((2-(trimethylsilyl)ethoxy)methyl)-4,5-dihydro-2H-benzo[e]indazol-7-amine

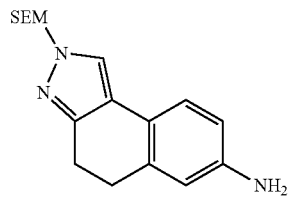

Intermediate 1A. 6-bromo-1-(((dimethylamino)methylene)-3,4-dihydronaphthalen-2(1H)-one

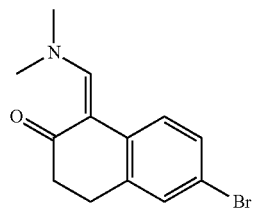 [SMILES: CN(C)/C=C1\C(=O)CCc2cc(Br)ccc21]

6-Bromo-3,4-dihydronaphthalen-2(1H)-one (100 mg, 0.44 mmol) in a RBF was added 1,1-dimethoxy-N,N-dimethylmethanamine (529 mg, 4.44 mmol) and 4-methylbenzenesulfonic acid hydrate (1.7 mg, 8.9 μmol). The reaction was stirred at rt for 1 hr. The reaction was concentrated and purified by flash chromatography (24 g column, 0-100%

EtOAc gradient in hexanes) to afford intermediate 1A (95 mg, 76%). ¹H NMR (400 MHz, CHLOROFORM-d) δ 7.83 (s, 1H), 7.26-7.19 (m, 2H), 6.63 (d, J=7.9 Hz, 1H), 2.90 (s, 6H), 276-2.63 (m, 2H), 2.41-2.30 (m, 2H). LCMS [M+H]⁺=280.0.

Intermediate 1B.
7-bromo-4,5-dihydro-2H-benzo[e]indazole

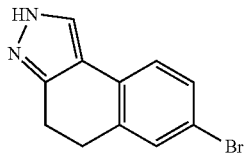 [SMILES: Brc1ccc2c(c1)CCc1n[nH]cc1-2]

To a solution of intermediate 1A (4.8 g, 17.1 mmol) in MeOH (170 mL) was added hydrazine, H₂O (2.14 g, 42.8 mmol). The reaction was stirred at rt overnight. It was concentrated and purified by flash chromatography (120 g column, 0-70% EtOAc/hexanes gradient) to give the desired Intermediate 1B (2.78 g, 65%). ¹H NMR (400 MHz, CHLOROFORM-d) δ 7.67 (s, 1H), 7.27 (s, 1H), 7.24-7.20 (m, 1H), 7.16-7.11 (m, 1H), 2.92-2.79 (m, 4H). LCMS [M+H]=250.9.

Intermediate 1C. 7-bromo-2-((2-(trimethylsilyl)ethoxy)methyl)-4,5-dihydro-2H-benzo[e]indazole

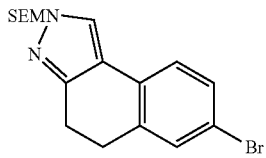 [SMILES: C[Si](C)(C)CCOCn1cc2c(n1)CCc1cc(Br)ccc1-2]

To a solution of intermediate 1B (3.45 g, 13.9 mmol) in THF (138 mL) at 0° C. was added 60% sodium hydride (0.775 g, 19.4 mmol). The reaction was stirred at 0° C. for 20 min, then (2-(chloromethoxy)ethyl)trimethylsilane (2.70 mL, 15.2 mmol) was added dropwise and the reaction was warmed slowly to rt overnight. Then, MeOH was added and the mixture was concentrated and purified by flash chromatography (120 g column, 0-50% EtOAc in hexanes) to afford intermediate 1C as a pale yellow oil (4.43 g, 84%). ¹H NMR (400 MHz, CHLOROFORM-d, 1:1 mixture of SEM regioisomers) δ 7.74 (s, 1H), 7.40-7.30 (m, 2H), 7.29-7.19 (m, 1H), 5.44 (s, 2H), 3.65-3.55 (m, 2H), 3.05-2.85 (m, 4H), 0.99-0.85 (m, 2H), 0.00 (s, 9H). LCMS, [M+H]⁺=380.9.

Intermediate 1. 2-((2-(trimethylsilyl)ethoxy)methyl)-4,5-dihydro-2H-benzo[e]indazol-7-amine The mixture of intermediate 1C (1.08 g, 2.85 mmol), copper(I) iodide (0.054 g, 0.29 mmol), L-proline (0.066 g, 0.57 mmol) and potassium carbonate (1.18 g, 8.54 mmol) in DMSO (11.4 mL) was degassed (vacuumed and back-filled with argon three times), then ammonium hydroxide (0.515 mL, 3.70 mmol) (28% aq) was added. The reaction mixture was capped and heated at 85° C. overnight. The reaction was diluted with EtOAc, washed with 1-120 and brine, dried over MgSO₄, filtered and concentrated. Purification by flash chromatography (80 g column, 0-60% EtOAc in H-exanes) provided intermediate 1 as a yellow oil (0.52 g, 58%). ¹H NMR (400 MHz, CHLOROFORM-d, 1:1 mixture of SEM regioisomers) δ 7.69 (s, 1H), 7.22 (dd, J=17.1, 7.8 Hz, 1H), 6.63-6.51 (m, 2H), 5.44 (s, 2H), 3.82-3.64 (brs, 2H), 3.63-3.52 (m, 2-1H), 3.01-2.83 (m, 41H), 0.98-0.86 (nm, 2H), 0.03-0.01 (s, 9H). LCMS [M+H]⁺=316.1.

Intermediate 2. 7-bromo-2-(4-methoxybenzyl)-4,5-dihydro-2H-benzo[e]indazole

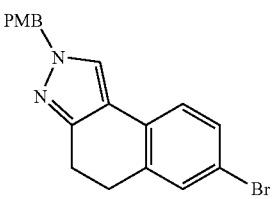

Intermediate 2 was prepared according to the similar procedure described in intermediate 1, except to use PMBCl in the step intermediate 1C. LCMS [M+H]⁺=369.2.

Intermediate 3. 7-bromo-1-methyl-3-((2-(trimethylsilyl)ethoxy)methyl)-4,5-dihydro-3H-benzo[e]indazole Intermediate 3A.
1-acetyl-6-bromo-3,4-dihydronaphthalen-2(1H)-one To a suspension of 60% sodium hydride (71.1 ng, 1.78 mmol) in DMSO (1.8 mL) was added 6-bromo-3,4-dihydronaphthalen-2(1H)-one (200 mg, 0.889 mmol). Then, 1-(1H-imidazol-1-yl)ethanone (117 mg, 1.07 mmol) was added. The reaction was stirred at rt for 20 min. The reaction was diluted with EtOAc, washed with 1N HCl and brine, dried over MgSO₄. It was filtered and concentrated. Purification by flash chromatography (24 g column, 0-40% EtOAc in Hexanes) afforded intermediate 3A as a pale yellow solid (163 mg, 69%). ¹H NMR (400 MHz, CHLOROFORM-d) δ 7.32-7.24 (m, 2H), 6.97 (d, J=9.0 Hz, 1H), 2.80-2.71 (m, 2H), 2.51-2.42 (m, 2H), 2.28 (s, 3H). LCMS [M+H]⁺=268.9.

Intermediate 3B. 7-bromo-1-methyl-4,5-dihydro-3H-benzo[e]indazole

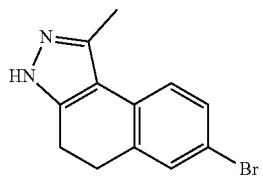

Intermediate 3B was prepared according to the similar procedure described in intermediate 1, except to use intermediate 3A in the step intermediate 1B. $^1$H NMR (400 MHz, CHLOROFORM-d) δ 7.33-7.26 (m, 2H-1), 7.25-7.20 (m, 1H), 2.92-286 (m, 2H), 2.82-2.74 (m, 2H), 2.46 (s, 3H). LCMS [M+H]$^+$=264.9.

Intermediate 3. 7-bromo-1-methyl-3-((2-(trimethylsilyl)ethoxy)methyl)-4,5-dihydro-3H-benzo[e]indazole Intermediate 3 was prepared according to the similar procedure described in intermediate 1C, except to use intermediate 3B in the step intermediate 1B. $^1$H NMR (400 MHz, CHLOROFORM-d, 1:1 mixture of SEM regioisomers) δ 7.43-724 (m, 3H), 5.44 (s, 2H), 3.61 (td, =8.1, 4.2 Hz, 2H), 3.04-2.75 (m, 4H), 2.59 (s, 3H), 0.93 (td, J=8.2, 4.7 Hz, 2H), 0.00 (s, 9H). LCMS [M+H]$^+$=395.0.

Intermediate 4. 2-((2-(trimethylsilyl)ethoxy)methyl)-2,4-dihydrochromeno[3,4-c]pyrazol-7-amine

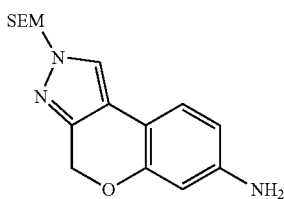

Intermediate 4A. Methyl 4-bromo-1((2-(trimethylsilyl)ethoxy)methyl)-1H-pyrazole-3-carboxylate

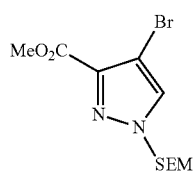 [SMILES: COC(=O)c1nn(COCC[Si](C)(C)C)cc1Br]

To a suspension of methyl 4-bromo-1H-pyrazole-3-carboxylate (2.45 g, 11.9 mmol) in THF (120 mL) at 0° C., was added 60% NaH (0.621 g, 15.5 mmol) portionwise. The reaction was stirred at 0° C. for 10 min, then 2-(trimethylsilyl)ethoxymethyl chloride (2.54 mL, 14.34 mmol) was added dropwise. The suspension was warmed slowly to rt overnight. Then, it was cooled down to 0° C., MeOH was added and the solvents were removed in vacuo. The residue was diluted with EtOAc and sat. NaHCO$_3$. The aqueous layer was extracted 2× with EtOAc. The organic layer was washed with brine, dried over MgSO$_4$ and concentrated. Purification by flash chromatography (80 g column, 0-50% EtOAc in Hexanes) afforded intermediate 4A as a colorless oil (3.17 g, 87%). $^1$H NMR (400 MHz, CHLOROFORM-d) δ 7.73 (s, IT), 5.48 (s, 2H), 3.97 (s, 3H), 3.63-3.56 (m, 2H), 0.93 (t, 1=8.3 Hz, 2H), 0.00 (s, 9H). LCMS [M+H]$^+$=337.0.

Intermediate 4B. (4-bromo-1-((2-(trimethylsilyl)ethoxy)methyl)-1H-pyrazol-3-yl)methanol

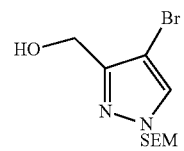

To a solution of methyl 4-bromo-1-((2-(trimethylsilyl)ethoxy)methyl)-1H-pyrazole-3-carboxylate (218 mg, 0.65 mmol) in THF (6.5 mL) at 0° C., was added a 2M solution of lithium borohydride (975 µl, 1.95 mmol). The reaction was slowly warmed to rt and stirred at rt overnight. The mixture was concentrated, diluted with EtOAc, washed with NaHCO$_3$ and brine, dried over MgSO$_4$, filtered and concentrated. Purification by flash chromatography (24 g column, 0-100% EtOAc in Hexanes) gave intermediate 4Bas a colorless oil (176 mg, 88%). $^1$H NMR (400 MHz, CHLOROFORM-d) δ 7.58 (s, 1H), 5.37 (s, 2H), 4.70 (d, J=5.9 Hz, 2H), 3.62-3.52 (m, 2H), 2.04-1.92 (br, 1H), 0.98-0.87 (m, 2H), 0.00 (s, 9H). LCMS [M+H]$^+$=308.9.

Intermediate 4C. (4-(2-fluoro-4-nitrophenyl)-1-((2-(trimethylsilyl)ethoxy)methyl)-1H-pyrazol-3-yl)methanol

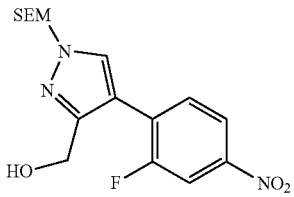 [SMILES: C[Si](C)(C)CCOCn1cc(-c2ccc([N+](=O)[O-])cc2F)c(CO)n1]

To a solution of intermediate 4B and 2-(2-fluoro-4-nitrophenyl)-4,4,5,5-tetramethyl-1,3,2-dioxaborolane (199 mg, 0.745 mmol) in THF (5.7 mL) was added 3M aq. K$_3$PO$_4$ (573 µl, 1.72 mmol). The mixture was bubbled with Ar for a few minutes and (DtBPF)PdCl$_2$ (37.3 mg, 0.057 mmol) was added. The reaction was heated at 90° C. overnight. The reaction was concentrated, diluted with EtOAc, washed with H$_2$O, back extracted with EtOAc. The combined organic layers were washed with brine, dried over MgSO$_4$, filtered and concentrated. Purification by flash chromatography (40 g column, 0-100% EtOAc in hexanes) gave intermediate 4C as a light brown oil (164 mg, 78%). $^1$H NMR (400 MHz, CHLOROFORM-d, 1:1 mixture of SEM regioisomers) δ 8.29 (dd, J=12.8, 1.8 Hz, 1H), 8.19 (dd, J=8.6, 2.2 Hz, 1H), 7.97-7.92 (m, 1H), 7.84 (t, J=8.3 Hz, 1H), 5.46 (d, J=2.6 Hz, 2H), 4.81 (br t, J=5.1 Hz, 2H), 3.68-3.61 (m, 2H), 2.40 (br s, 1H), 0.99-0.92 (m, 2H), 0.0 (s, 9H). LCMS [M+H]$^+$368.1.

Intermediate 4D. 7-nitro-2-((2-(trimethylsilyl)ethoxy)methyl)-2,4-dihydrochromeno[3,4-c]pyrazole

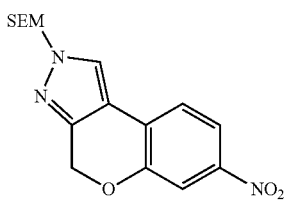 [SMILES: C[Si](C)(C)CCOCn1cc2c(n1)COc1cc([N+](=O)[O-])ccc1-2]

To a solution of intermediate 4C (164 mg, 0.446 mmol) in DMF (4.5 mL), was added cesium carbonate (436 mg, 1.34 mmol). The reaction was heated at 100° C. for 4 h, then cooled down to rt overnight. The mixture was diluted with EtOAc, washed with H$_2$O and brine, dried over MgSO$_4$, filtered and concentrated. Purification by flash chromatography (12 g column, 0-50% EtOAc in hexanes) gave intermediate 4D as a yellow solid (63.9 mg, 41%). $^1$H NMR (400 MHz, CHLOROFORM-d) δ 7.89-7.80 (m, 3H), 7.42 (d, J=8.4 Hz, 1H), 5.46 (s, 2H), 5.38 (s, 2H), 3.67-3.57 (m, 2H), 1.00-0.89 (m, 2H), 0.00 (s, 9H). LCMS [M+H]$^+$=348.1.

Intermediate 4. 2-((2-(trimethylsilyl)ethoxy)methyl)-2,4-dihydrochromeno[3,4-c]pyrazol-7-amine To a solution of intermediate 4D (89 mg, 0.256 mmol) in ethyl acetate (1.3 mL)/MeOH (1.3 mL), was added ammonium chloride (137 mg, 2.56 mmol) and zinc (167 mg, 2.56 mmol). The mixture was stirred at rt overnight. The reaction mixture was filtered, rinsed with EtOAc and concentrated. Purification by flash chromatography (12 g column, 0-100% EtOAc in Hexanes) gave intermediate 4 as a yellow oil (70 mg, 86%). $^1$H NMR (400 MHz, CHLOROFORM-d) δ 7.61-7.50 (m, 1H), 7.17-7.09 (m, 1H), 6.44-6.27 (m, 2H), 5.46-5.37 (m, 2I-1H), 5.28-5.20 (m, 2H), 3.63-3.52 (m, 2I-1H), 0.94 (dd, J=8.9, 7.8 Hz, 2H), 0.0 (s, 9) LCMS, [M+H]$^+$=318.1.

Intermediate 5. 2-((2-(trimethylsilyl)ethoxy)methyl)-2,4-dihydropyrazolo[4',3':4,5]pyrano[2,3-b]pyridin-7-amine

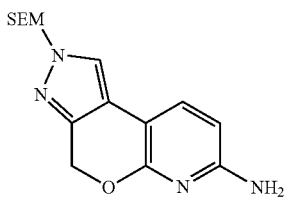 [SMILES: C[Si](C)(C)CCOCn1cc2c(n1)COc1nc(N)ccc1-2]

Intermediate 5 was prepared according to the similar procedure described in intermediate 4, except to use 6-fluoro-5-(4,4,5,5-tetramethyl-1,3,2-dioxaborolan-2-yl)pyridin-2-amine in the step intermediate 4C. LCMS [M+H]= 319.2.

Example 1

(rac)-1'-(4,5-dihydro-2H-benzo[e]indazol-7-yl)spiro[indoline-2,3'-pyrrolidin]-2'-one

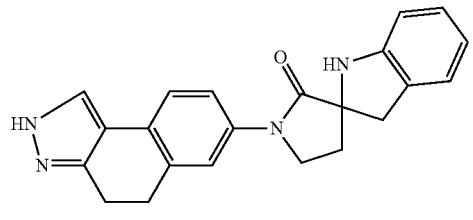 [SMILES: O=C1N(c2ccc3c(c2)CCc2n[nH]cc2-3)CCC12Cc1ccccc1N2]

Example 1A. 1-(tert-butyl) 2-methyl 2-allylindoline-1,2-dicarboxylate

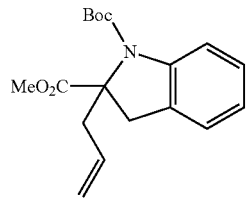 [SMILES: C=CCC1(C(=O)OC)Cc2ccccc2N1C(=O)OC(C)(C)C]

To a solution of 1-tert-butyl 2-methyl indoline-1,2-dicarboxylate (2.0 g, 7.21 mmol) in THF (30 mL), was added NaHMDS (14.4 mL, 1M in THF, 14.4 mmol) dropwise. The mixture was stirred at −30° C. for 30 min, then cool to −78° C., and allyl bromide (2.00 mL, 23.1 mmol) was added slowly. The reaction mixture was warmed up to rt and stirred for 2 h. The mixture was quenched with sat. NH$_4$Cl, extract 2× with EtOAc. Organic layer was concentrated and the crude mixture was purified by flash chromatography (120 g column, Hexane:EtOAC 0-20%) to give example LA (1.73 g, 76% yield) as a yellow oil. $^1$H NMR (400 MHz, CHLOROFORM-d) δ 7.89 (br. s., 1H), 7.19 (t, J=7.4 Hz, 1H), 7.07 (d, J=6.8 Hz, 1H), 6.98-6.89 (m, 1H), 5.72-5.53 (m, 1H), 5.13 (d, J=16.9 Hz, 1H), 5.02 (d, J=10.1 Hz, 1H), 3.74 (s, 3H), 3.40-3.16 (m, 2H), 3.07 (br. s., 1H), 2.72 (dd, J=14.4, 7.6 Hz, 1H), 1.51 (br. s., 9H). LCMS [M+H−Boc]$^+$=218.1.

Example 1B. 1-(tert-butyl) 2-methyl 2-(2-oxoethyl)indoline-1,2-dicarboxylate

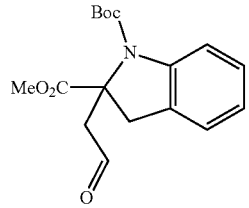 [SMILES: COC(=O)C1(CC=O)Cc2ccccc2N1C(=O)OC(C)(C)C]

To a solution of example 1A (0.902 g, 2.84 mmol) in MeOH (50 mL) and water (25 mL) was added osmium tetroxide (2.5% in t-BuOH) (2.50 mL, 0.199 mmol). After 5 min, sodium periodate (1.82 g, 8.53 mmol)) was added. The reaction was stirred at rt for 2 h. The mixture was added to water and extract 2× with EtOAc. The combined organic layers were washed with water and brine, concentrated then purified by flash chromatography (40 g column, 0-60% EtOAc in Hexanes) to give example 1B (688 µg, 76% yield) as a grey oil. ¹H NMR (400 MHz, CHLOROFORM-d) δ 9.82 (br. s., 1H), 8.03-7.36 (m, 1H), 7.22 (t, J=7.6 Hz, 1H), 713 (d, J=7.5 Hz, 1H), 7.04-6.92 (m, 1H), 3.78 (s, 3H), 3.59-3.29 (m, 2H), 3.22 (dd, J=15.3, 3.2 Hz, 1H), 2.98 (d, J=13.4 Hz, 1H), 1.66-1.45 (m, 9H). LCMS [M+H–Boc]⁺=320.1.

Example 1C. 1-(tert-butyl) 2-methyl 2-(2-((2-((2-(trimethylsilyl)ethoxy)methyl)-4,5-dihydro-2H-benzo[e]indazol-7-yl)amino)ethyl)indoline-1,2-dicarboxylate

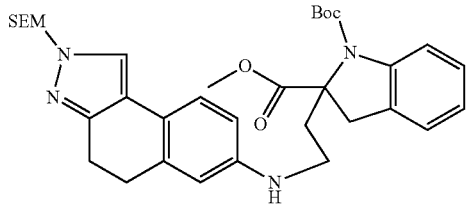 [SMILES: COC(=O)C1(CCNc2ccc3c(c2)CCc2nn(COCC[Si](C)(C)C)cc2-3)Cc2ccccc2N1C(=O)OC(C)(C)C]

A solution of Intermediate 1 (54 mg, 0.171 mmol) and example 1B (54.7 mg, 0.171 mmol) in MeOH (856 µl) was stirred at rt for 40 min, 1M sodium cyanoborohydride (342 µl, 0.342 mmol) in THF was added dropwise and the reaction was stirred at rt overnight. Then, a few drops of 1N NaOH was added and the mixture was concentrated. The mixture was diluted with EtOAc, washed with sat. NaHCO₃ and brine, and dried over MgSO₄. The mixture was filtered and concentrated. Purification by flash chromatography (24 g column, 0-50% EtOAc in Hexanes) gave example 1C as a yellow solid (51 mg, 48%). ¹H NMR (400 MHz, CHLOROFORM-d) δ 8.00 (br s, 1H), 7.69-7.57 (m, 1H), 7.34-7.11 (m, 3H), 7.08-6.97 (m, 1H), 6.45-6.38 (m, 2H), 5.43 (d, J=14.3 Hz, 2H), 3.78 (s, 3H), 3.67-3.44 (m, 4H), 333-3.15 (m, 3H), 3.01-2.84 (m, 4H), 2.31 (dt, J=14.3, 7.1 Hz, 1H), 1.50 (br s, 9H), 0.97-0.84 (m, 4H), 0.00 (s, 9H). LCMS [M+H]⁺=619.3.

Example 1D. tert-butyl 2'-oxo-1'-(2-((2-(trimethylsilyl)ethoxy)methyl)-4,5=dihydro-2H-benzo[e]indazol-7-yl)spiro[indoline-2,3'-pyrrolidine]-1-carboxylate

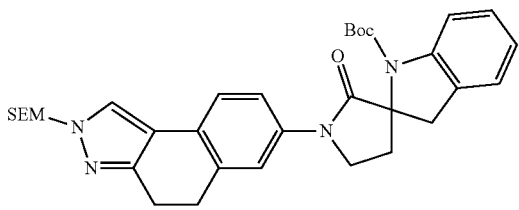 [SMILES: CC(C)(C)OC(=O)N1c2ccccc2CC12CCN(c1ccc3c(c1)CCc1nn(COCC[Si](C)(C)C)cc1-3)C2=O]

To a solution of example 1C (51 mg, 0.082 mmol) in THF (824 µL) at 0° C. was added 60% sodium hydride (6.6 mg, 0.165 mmol). The reaction was warmed up to rt then to 65° C. for 1 h. The reaction was cooled to rt, and MeOH was added to quench the reaction. It was concentrated and purified by flash chromatography (12 g column, 0-50% EtOAc in Hexanes) to give example 1D as an off-white solid (26.5 mg, 55%). ¹H NMR (400 MHz, CHLOROFORM-d) δ 7.94 (br s. 1H), 7.74 (d, J=13.6 Hz, 1H), 7.68-7.58 (m, 1H), 7.56-7.33 (m, 2H), 7.22 (br t, J=7.4 Hz, 1H), 7.13 (d, J=7.3 Hz, 1H), 7.02-6.93 (m, 1H), 5.43 (d, J=12.5 Hz, 2H), 3.88 (br s, 2H), 3.67-3.49 (m, 3H), 3.17-3.01 (m, 3H), 2.94 (dq, J=14.0, 7.1 Hz, 2H) 2.76 (br d, J=8.6 Hz, 1H), 2.30 (br s, 1H). 1.55-1.35 (br s, 9H), 0.99-0.78 (m, 2H), 0.00 (s, 9H). LCMS [M+H]⁺=587.2.

Example 1E. tert-butyl 1-(4,5-dihydro-2H-benzo[e]indazol-7-yl)-2'-oxospiro[indoline-2,3'-pyrrolidine]-1-carboxylate

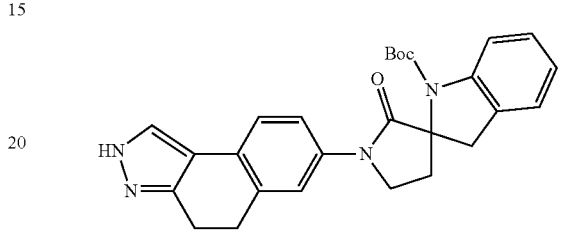

To a solution of example 1D (10 mg, 0.017 mmol) in THF (0.4 mL) was added 1M TBAF (0.085 mL, 0.085 mmol). The reaction was heated at 70° C. overnight. Then, the mixture was concentrated and purified by flash chromatography (4 g column, 0-100% EtOAc in Hexanes) to give example 1E as a white solid (7 mg, 86%). ¹H NMR (400 MHz, CHLOROFORM-d) δ 7.86 (br s, 11-), 7.71-7.61 (m, 1H), 7.60-7.42 (m, 2H), 7.40-7.22 (m, 1H) 7.14 (br t, J=6.9 Hz, 1H), 7.05 (d, J=7.3 Hz, 1H), 7.01-6.84 (m, 1H), 3.94-3.71 (m, 2H), 3.46 (br d, J=15.6 Hz, 1H), 3.10-2.91 (m, 3H), 2.86 (br s, 2H), 2.75-2.61 (m, 1H), 2.22 (br d, J=0.9 Hz, 1H), 1.60-1.33 (m, 9H). LCMS [M+H]⁺=457.1.

Example 1

To a solution of Example 1E (13.5 mg, 0.030 mmol) in DCM (0.25 mL), was added TFA (0.228 mL, 2.96 mmol) and the reaction was stirred at rt for 10 min. The reaction was concentrated and purified by prep-HPLC (CH₃CN/H₂O/0.1% TFA system) to give example 1 as an off-white solid (8.5 mg, 61%). LCMS [M+H]⁺=357.1. ¹H NMR (400 MHz, METHANOL-d₄) δ 8.05 (br. s., 1H), 7.66-7.59 (m, 1H), 7.58-7.49 (m, 2H), 7.10 (d, J=7.3 Hz, 1H), 7.04 (t, J=7.5 Hz, 1H), 6.79-6.66 (m, 2H), 3.96-3.84 (m, 2H), 3.11-3.02 (m, 2H), 2.97-2.89 (m, 2H), 2.49-2.25 (m, 2H), 1.51-1.22 (m, 2H). Analytical HPLC: RT=6.16 min (Method C); 8.07 min (Method D).

Example 2

1-(4,5-dihydro-2H-benzo[e]indazol-7-yl)-3-(3-methoxybenzyl)imidazolidin-2-one

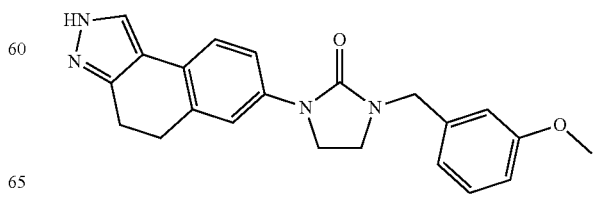

Example 2A.
1-(3-methoxybenzyl)imidazolidin-2-one

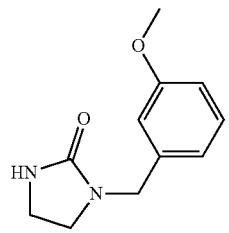

To a solution of imidazolidin-2-one (0.427 g, 4.49 mmol) in DMF (22.4 mL), was added 1M LiHMDS (4.49 mL, 4.49 mmol) and stirred for 2 hours. To this mixture was added 1-(bromomethyl)-3-methoxybenzene (0.902 g, 4.49 mmol) and it was stirred over 48 h. The reaction was diluted with MeOH and concentrated. The residue was partitioned between $H_2O$ and EtOAc, extracted with EtOAc (3×), and the organic phase was dried over $MgSO_4$, filtered and concentrated. Purification by flash chromatography (24 g column, 0-100% EtOAc in Hexanes) gave example 2A as a white solid (620 mg, 67%). $^1$H NMR (400 MHz, CHLOROFORM-d) δ 6.89-6.65 (m, 3H), 4.27 (s, 2H), 3.73 (s, 3H), 3.41-3.30 (m, 2H), 3.29-3.17 (m, 2H). LCMS $[M+H]^+$=207.1.

Example 2B. 1-(3-methoxybenzyl)-3-(2-(4-methoxybenzyl)-4,5-dihydro-2H-benzo[e]indazol-7-yl)imidazolidin-2-one

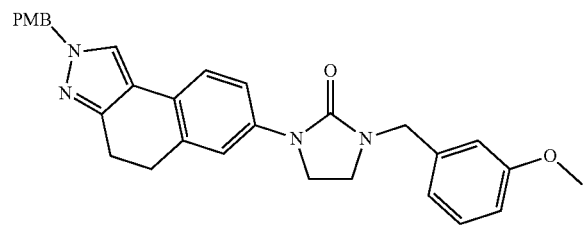

To a degassed solution of example 2A (29 mg, 0.060 mmol) and Intermediate 2 (14.9 mg, 0.072 mmol) in THF (600 μL), was added $Pd_2(dba)_3$ (1.1 mg, 1.2 μmol), Xantphos (1.0 mg, 1.8 μmol), $Cs_2CO_3$ (27.4 mg, 0.084 mmol). The reaction was heated at 90° C. overnight. The mixture was concentrated. To the residue was added $DMF/CH_3CN$, and the mixture was filtered and purified by prep HPLC ($CH_3CN/H_2O/0.1$% TFA system, 0-100%) to give example 2B as a yellow oil (24 mg, 66%) LCMS $[M+H]^+$=495.4.

Example 2

To Example 2B (22 mg, 0.036 mmol) in a microwave tube was added TFA (361 μl). The tube was sealed and healed at 130° C. for 7 h, then cooled to rt overnight. TFA was removed and DMF/MeOH was added. The mixture was filtered and purified by reverse phase HPLC ($CH_3CN$/1-120/0. % TFA system, 0-100%) to give example 2 as a white solid (9.4 mg, 53%). $^1$H NMR (400 MHz, METHANOL-$d_4$) δ 8.03 (s, 1H), 7.56-7.39 (m, 3H), 7.27 (t, J=7.9 Hz, 1H), 6.99-6.80 (m, 3H), 4.43 (s, 2H), 3.93-3.83 (m, 2H), 3.81-3.73 (m, 3H), 3.49-3.37 (m, 2H), 3.11-3.00 (m 2H), 299-2.88 (m, 2H). LCMS $[M+H]^+$=375.3. Analytical HPLC: RT=6.66 min (Method C); 8.57 min (Method D).

Example 3

(S)-1-(4,5-dihydro-21-benzo[e]indazol-7-yl)-3-((3-methoxyphenyl)amino)pyrolidin-2-one

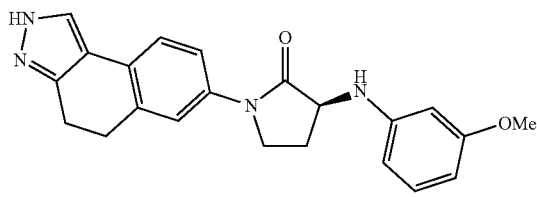 [SMILES: COc1cccc(N[C@H]2CCN(c3ccc4c(c3)CCc3n[nH]cc3-4)C2=O)c1]

Example 3A. (R)-3-hydroxy-1-(2-(4-methoxybenzyl)-4,5-dihydro-2H-benzo[e]indazol-7-yl)pyrrolidin-2-one

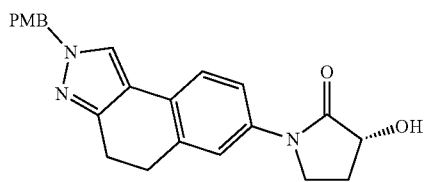

A solution of intermediate 2 (65 mg, 0.176 mmol), (R)-3-hydroxypyrrolidin-2-one (21.4 mg, 0211 mmol) and $Cs_2CO_3$ (80 mg, 0.25 mmol) in THF (1.76 mL) was degassed by bubbling with Ar and was added $Pd_2(dba)_3$ (6.5 mg, 7.0 μmol) and Xantphos (6.1 mg, 10.6 mmol). The reaction was heated at 100° C. overnight. The mixture was filtered and concentrated. Purification by flash chromatography (24 g column, 0-10% MeOH in DCM) gave example 3A as a yellow solid (46.1 mg, 67%). $^1$H NMR (400 MHz, CHLOROFORM-d, 2:1 mixture of regio isomers, major one reported) δ 7.46-7.43 (m, 1H), 7.41 (s, 1H), 7.37-7.33 (m, 1H), 7.21-7.19 (m, 1H), 7.17 (d, J=8.6 Hz, 2H), 6.82 (d, J=8.6 Hz, 2H), 5.15 (s, 2H), 4.43-4.35 (m, 1H), 375-3.73 (m, 4H), 3.06 (br s, 1H), 2.97-2.89 (m, 2H), 2.85-2.80 (m, 2H) 2.53 (dddd, J=12.5, 8.1, 6.1, 2.0 Hz, 1H), 2.02 (dd, J=12.5, 9.5 Hz, 1H). LCMS $[M+H]^+$=390.1.

Example 3B, (R)-1-(2-(4-methoxybenzyl)-4,5-dihydro-2H-benzo[e]indazol-7-yl)-2-oxopyrrolidin-3-yl methanesulfonate

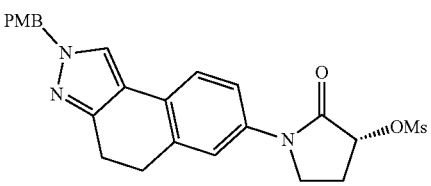

To a solution of example 3A (46 ng, 0.118 mmol) in DCM (1.2 mL) was added DIPEA (61.9 μL, 0.354 mmol) and cooled to 0° C. Methanesulfonyl chloride (13.8 μL, 0.177 mmol) was added and stirred at rt for 2 h. The reaction mixture was diluted with DCM, washed with sat. NaHCO$_3$, water and brine, dried over MgSO$_4$ and filtered and concentrated to give yellow solid which was used in the next step without purification. LCMS [M+H]$^+$=468.1.

Example 3C. (S)-1-(2-(4-methoxybenzyl)-4,5-di-hydro-2H-benzo[e]indazol-7-yl)-3-((3-methoxyphenyl)amino)pyrrolidin-2-one

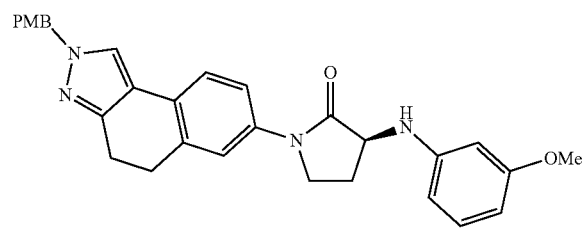

To a solution of example 3B (62 mg, 0.133 mmol) in THF (663 μL) was added 3-methoxyaniline (32.7 ng, 0.265 mmol), sodium acetate trihydrate (54.1 mg, 0.398 mmol) and water (663 μL). The reaction was heated at 80° C. overnight. The mixture was diluted with EtOAc, washed with H$_2$O and brine, dried over MgSO$_4$, filtered and concentrated. Purification by flash chromatography (12 g column, 0-70% EtOAc in Hexanes) gave Example 3C (32.8 mg, 50%) as a pale yellow solid. $^1$H NMR (400 MHz, CHLOROFORM-d, 2:1 mixture of PMB regioisoners, major isomer reported) δ 7.47 (d, J=2.2 Hz, 1H), 7.41 (s, 1H), 7.39-7.25 (m, 1H), 7.24-7.12 (m, 2H), 7.08-7.01 (m, 2H), 6.86-6.73 (m, 2H), 6.27 (td, J=8.1, 1.9 Hz, 2H), 6.19 (t, J=2.2 Hz, 1H), 5.14 (s, 2H), 4.10-3.99 (m, 2H), 3.82-3.74 (m, 2H), 3.71 (s, 3H), 3.00-2.89 (m, 2H), 2.87-2.62 (m, 3H), 1.96-1.85 (m, 1H). LCMS [M+H]$^+$=495.2.

Example 3

A solution of example 3C (32 mg, 0.065 mmol) and anisole (35.3 μL, 0.324 mmol) in TFA (647 μl) in a sealed tube was heated at 130° C. for 5 h. The reaction was cooled down to rt and stirred at it overnight. Then, TFA was removed and the mixture purified by prep HPLC (CH$_3$CN/H$_2$O/0.1% TFA, 0-100%) and Chiral SFC to give Example 3 as a light yellow solid (2.5 mg, 10%). $^1$H NMR (400 MHz, METHANOL-d$_4$) δ 8.09 (s, 1H), 7.64 (s, 1H), 7.56 (d, J=0.9 Hz, 2H), 7.20-7.10 (m, 1H), 6.58-6.42 (m, 3H), 4.51-4.43 (m, 1H), 4.03-3.86 (m, 2H), 3.80 (s, 31H), 3.14-3.06 (m, 2H), 3.00-2.93 (m, 2H), 2.71 (dt, J=12.5, 6.5 Hz, 1H), 2.16-2.01 (m, 1H). LCMS [M+H]$^+$=375.1. Analytical HPLC: RT=6.61 min (Method C); 8.52 min (Method D).

Example 4

(R)-2-amino-N-(4,5-dihydro-2H-benzo[e]indazol-7-yl)-4-phenylbutan amide

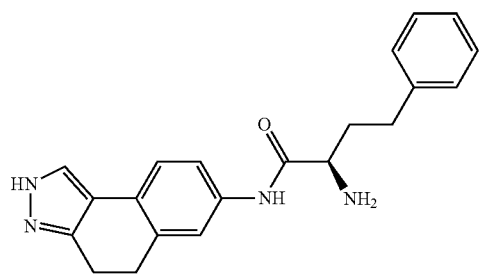 [SMILES: N[C@H](CCc1ccccc1)C(=O)Nc1ccc2c(c1)CCc1n[nH]cc1-2]

Example 4A. tert-butyl (R)-(1-oxo-4-phenyl-1-((2-((2-(trimethylsilyl)ethoxy)methyl)-4,5-dihydro-2H-benzo[e]indazol-7-yl)amino)butan-2-yl)carbamate

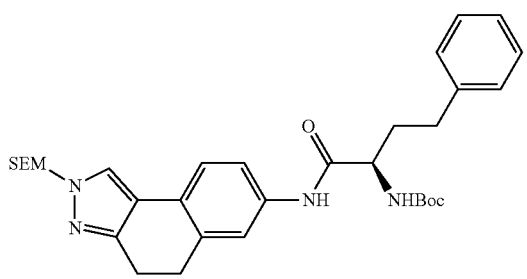 [SMILES: CC(C)(C)OC(=O)N[C@H](CCc1ccccc1)C(=O)Nc1ccc2c(c1)CCc1nn(COCC[Si](C)(C)C)cc1-2]

To a solution of intermediate 1 in DMF (0.6 mL) was added (R)-2-((tert-butoxycarbonyl)amino)-4-phenylbutanoic acid (16.8 rag, 0.060 mmol), DIEA (26 μL, 0.15 mmol) and HATU (25.2 mg, 0.066 mmol) at 0° C. The reaction was stirred under argon at 0° C. for 1.5 hrs. The reaction mixture was diluted with EtOAc, washed with 1-120 and brine. The organic phase was dried over MgSO$_4$, filtered and concentrated. The crude product was purified by flash chromatography (12 g column, eluting with 0% to 100% ethyl acetate/hexane) to give example 4A as a colorless oil (23 mg, 66%). $^1$H NMR (500 MHz, CHLOROFORM-d, mixture of SEM regioisomers, major one reported) δ 8.27 (br s, 1H), 7.72 (s, 1H), 7.54-7.42 (m, 1H), 7.37-7.14 (m, 7H), 5.41 (s, 2H), 5.17 (br d, J=7.7 Hz, 1H), 4.23 (br s, 1H), 3.65-3.55 (m, 2H), 3.04-2.84 (m, 4H), 2.78 (t, J=77.8 Hz, 2H), 2.34-2.22 (m, 1H), 2.05-1.96 (m, 1H), 1.49 (s, 9H), 0.97-0.89 (m, 2H), LCMS [M+H]$^+$=577.3.

Example 4

To a solution of example 4A (24 mg, 0.042 mmol) in THF (0.42 mL) was added 1M TBAF (208 μL, 0.208 mmol) and the reaction was stirred at 85° C. overnight. The mixture was concentrated and purified by flash chromatography (12 g column, 0-100% EtOAc in Hexanes and then 10% MeOH in DCM) to give the product. Then, this product was dissolved in 0.5 mL DCM and 0.2 mL TFA was added. The mixture was stirred at rt for 1 h and concentrated. Purification by prep HPLC (0-100% CH-3CN/H$_2$O with 0.1% TFA) provided Example 4 as an off-white solid (4 mg, 28%). $^1$H NMR (400 MHz, METHANOL-d$_4$) δ 7.96 (s, 1H), 7.53 (d, J=0.9 Hz, 1H), 7.50-7.44 (m, 2H), 7.35-7.19 (m, 5H), 4.11-4.06 (m, 1H), 3.08-3.01 (m, 2H), 2.96-2.90 (m, 2H), 2.80 (t, J=8.5 Hz, 2H), 2.36-2.17 (m, 2H). LCMS [M+H]$^+$= 3472. Analytical HPLC: RT=3.84 min (Method C); 6.15 min (Method D).

Example 5

1-(2,4-dihydropyrazolo[4',3':4,5]pyrano[2,3-b]pyridin-7-yl)-3-(3-methoxybenzyl)urea

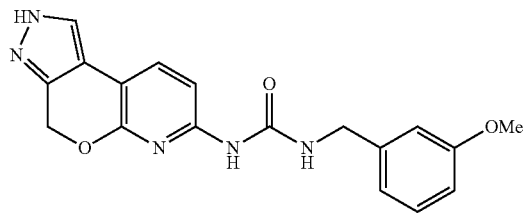 [SMILES: COc1cccc(CNC(=O)Nc2ccc3c(n2)OCc2n[nH]cc2-3)c1]

Example 5A. 1-(3-methoxybenzyl)-3-(2-((2-(trimethylsilyl)ethoxy)methyl)-2,4-dihydropyrazolo[4',3':4,5]pyrano[2,3-b]pyridin-7-yl)urea

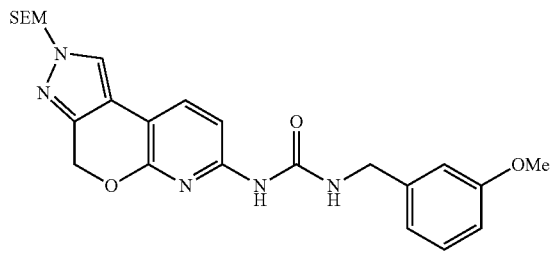 [SMILES: COc1cccc(CNC(=O)Nc2ccc3c(n2)OCc2nn(COCC[Si](C)(C)C)cc2-3)c1]

To a stirred solution of Intermediate 5 (100 mg, 0.314 mmol) in THF (1 mL) at rt, was added. 1-(isocyanatomethyl)-3-methoxybenzene (51.2 mg, 0.314 mmol) and the reaction was stirred at rt for 6 h. The reaction mixture was concentrated and the residue was triturated with hexane (10 mL). The red semisolid obtained was dried under vacuum and used in the next step without further purification. LCMS, [M+H]$^+$=482.4.

Example 5

To a stirred solution of example 5A (50 mg, 0.036 mmol) in DCM (1 mL) at 0° C. was added. TFA (0.028 mL, 0.36 mol). The cold bath was removed and the reaction was stirred at rt for 6 h. The reaction was concentrated and purified by prep HPLC to give Example 5 (10 mg, 78%). $^1$H NMR (400 MHz, DMSO-d$_6$) δ ppm 3.74 (s, 3H), 4.32-4.42 (m, 2H), 5.43 (s, 2H), 6.80-6.92 (m, 3H), 7.06-7.13 (m, 1H) 7.21-7.30 (m, 1H) 7.71-7.78 (m, 1H) 7.98-8.09 (m, 2H) 9.12-9.21 (m, 1H). LCMS [M+H]$^+$=352.1. HPLC: RT=1.30 min (Method A), 1.40 min (Method B).

The following examples in Table 1 were prepared using similar procedures to that which were used in the preparation of Example 1-3.

TABLE 1

| Example No. | Structure & Name | Analytical Data | Synthetic Method |
|---|---|---|---|
| 6 | 1'-(4,5-dihydro-2H-benzo[e]indazol-7-yl)spiro[indoline-2,3'-pyrrolidin]-2'-one (chiral) | $^1$H NMR (500 MHz, CHLOROFORM-d) δ 7.86 (s, 1H), 7.64 (d, J = 1.9 Hz, 1H), 7.47-7.42 (m, 1H), 7.40-7.32 (m, 1H), 7.14-7.03 (m, 2H), 6.83 (t, J = 7.4 Hz, 1H), 6.78 (d, J = 8.0 Hz, 1H), 3.89-3.75 (m, 2H), 3.49-3.39 (m, 2H), 3.06-2.94 (m, 4H), 2.47-2.30 (m, 2H). HPLC RT = 6.16 min (method C). LCMS [M + H]$^+$ = 357.1 | Example 1 |
| 7 | (R)-1-(4,5-dihydro-2H-benzo[e]indazol-7-yl)-3-(1-(3-methoxyphenyl)ethyl)imidazolidin-2-one | $^1$H NMR (400 MHz, METHANOL-d$_4$) δ 8.04 (s, 1H), 7.47 (d, J = 8.1 Hz, 2H), 7.43-7.37 (m, 1H), 7.31 (t, J = 7.9 Hz, 1H), 7.05-6.93 (m, 2H), 6.88 (dd, J = 8.3, 2.1 Hz, 1H), 5.26 (q, J = 7.1 Hz, 1H), 3.91-3.73 (m, 5H), 3.56 (d, J = 6.2 Hz, 1H), 3.17 (d, J = 6.8 Hz, 1H), 3.09-3.01 (m, 2H), 2.99-2.84 (m, 2H), 1.60 (d, J = 7.3 Hz, 3H). HPLC RT = 7.04 min (method C). LCMS [M + H]$^+$ = 389.1 | Example 2 |

| Example No. | Structure & Name | Analytical Data | Synthetic Method |
|---|---|---|---|
| 8 | 1-(4,5-dihydro-2H-pyrazolo[4,3-f]quinolin-7-yl)-3-(3-methoxybenzyl)imidazolidin-2-one | $^1$H NMR (400 MHz, METHANOL-d$_4$) δ 8.27 (d, J = 8.8 Hz, 1H), 8.09 (s, 1H), 7.55 (d, J = 8.8 Hz, 1H), 7.32 (t, J = 7.8 Hz, 1H), 6.99-6.89 (m, 3H), 4.54 (s, 2H), 4.14-4.05 (m, 2H), 3.86-3.79 (m, 3H), 3.63-3.56 (m, 2H), 3.16-3.08 (m, 2H). HPLC RT = 8.08 min (method C). LCMS [M + H]$^+$ = 376.2 | Example 2 |
| 9 | (R)-1-(4,5-dihydro-2H-benzo[e]indazol-7-yl)-3-((3-methoxyphenyl)amino)pyrrolidin-2-one (Chiral) | $^1$H NMR (400 MHz, METHANOL-d$_4$) δ 8.13 (s, 1H), 7.64 (s, 1H), 7.59-7.52 (m, 2H), 7.22-7.13 (m, 1H), 6.59-6.46 (m, 3H), 4.48 (dd, J = 10.1, 8.4 Hz, 1H), 4.01-3.86 (m, 2H), 3.80 (s, 3H), 3.14-3.04 (m, 2H), 3.02-2.93 (m, 2H), 2.76-2.62 (m, 1H), 2.09 (dq, J = 12.2, 9.7 Hz, 1H). HPLC RT = 6.62 min (method C). LCMS [M + H]$^+$ = 375.2 | Example 3 |
| 10 | 1-(2,4-dihydrochromeno[3,4-c]pyrazol-7-yl)-3-((3-methoxyphenyl)amino)pyrrolidin-2-one (Chiral) | $^1$H NMR (400 MHz, METHANOL-d$_4$) δ 7.91 (s, 1H), 7.46 (d, J = 8.4 Hz, 1H), 7.36 (d, J = 2.2 Hz, 1H), 7.31-7.21 (m, 1H), 7.15-7.04 (m, 1H), 6.51-6.35 (m, 2H), 5.27 (s, 2H), 4.42 (dd, J = 10.1, 8.1 Hz, 1H), 3.94-3.83 (m, 2H), 3.79-3.72 (m, 3H), 2.73-2.59 (m, 1H), 2.11-1.92 (m, 1H). HPLC RT = 7.16 min (method C). LCMS [M + H]$^+$ = 377.2 | Example 3 |
| 11 | 1-(2,4-dihydropyrazolo[4',3':4,5]pyrano[2,3-b]pyridin-7-yl)-3-((3-methoxyphenyl)amino)pyrrolidin-2-one (Racemate) | $^1$H NMR (400 MHz, DMSO-d6) δ ppm 13.00 (br. s., 1 H) 8.12 (s, 1 H) 7.86-8.01 (m, 2 H) 6.99 (t, J = 7.95 Hz, 1 H) 6.26-6.35 (m, 2 H) 6.17 (d, J = 8.56 Hz, 1 H) 5.93 (d, J = 7.58 Hz, 1 H) 5.48 (s, 2 H) 4.45 (q, J = 8.40 Hz, 1 H) 4.06 (t, J = 10.27 Hz, 1 H) 3.63-3.83 (m, 4 H) 2.54-2.61 (m, 1 H) 1.79-1.95 (m, 1 H). HPLC RT = 1.59 min (method A). LCMS [M + H]$^+$ = 378.1 | Example 3 |
| 12 | 1-(2,4-dihydropyrazolo[4',3':4,5]pyrano[2,3-b]pyridin-7-yl)-3-((3-fluoro-5-methoxyphenyl)amino)pyrrolidin-2-one (Racemate) | $^1$H NMR (400 MHz, DMSO-d$_6$) δ ppm 13.00 (br. s., 1 H) 8.12 (s, 1 H) 7.85-7.98 (m, 2 H) 6.29 (d, J = 7.58 Hz, 1 H) 6.08-6.16 (m, 2 H) 5.99 (d, J = 10.76 Hz, 1 H) 5.47 (s, 2 H) 4.44-4.54 (m, 1 H) 4.00-4.12 (m, 1 H) 3.64-3.81 (m, 4 H) 2.54-2.61 (m, 1 H) 1.78-1.92 (m, 1 H). HPLC RT = 1.71 min (method A). LCMS [M + H]$^+$ = 396.1 | Example 3 |

TABLE 1-continued

| Example No. | Structure & Name | Analytical Data | Synthetic Method |
|---|---|---|---|
| 13 | 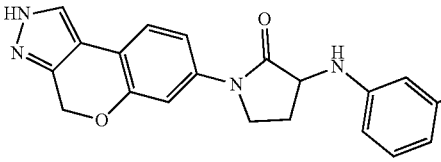<br>1-(2,4-dihydrochromeno[3,4-c]pyrazol-7-yl)-3-((3-methoxyphenyl)amino)pyrrolidin-2-one (Racemate) | $^1$H NMR (400 MHz, METHANOL-$d_4$) δ 7.93 (s, 1H), 7.47 (d, J = 8.4 Hz, 1H), 7.38 (d, J = 2.0 Hz, 1H), 7.28 (dd, J = 8.4, 2.2 Hz, 1H), 7.17 (t, J = 7.9 Hz, 1H), 6.64-6.42 (m, 3H), 5.29 (s, 2H), 4.47 (dd, J = 10.1, 8.4 Hz, 1H), 3.97-3.83 (m, 2H), 3.80-3.74 (m, 3H), 2.70-2.57 (m, 1H), 2.06 (dq, J = 12.4, 9.7 Hz, 1H)<br>HPLC RT = 7.18 min (method C).<br>LCMS [M + H]$^+$ = 377.2 | Example 3 |
| 14 | 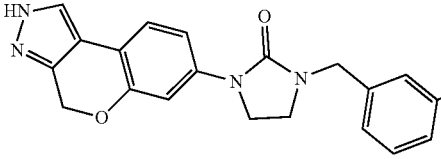<br>1-(2,4-dihydrochromeno[3,4-c]pyrazol-7-yl)-3-(3-methoxybenzyl)imidazolidin-2-one | $^1$H NMR (400 MHz, METHANOL-$d_4$) δ 7.86 (s, 1H), 7.40 (d, J = 8.4 Hz, 1H), 7.32-7.12 (m, 3H), 6.95-6.78 (m, 3H), 5.25 (s, 2H), 4.42 (s, 2H), 3.84 (dd, J = 9.1, 7.2 Hz, 2H), 3.79 (s, 3H), 3.44-3.36 (m, 2H).<br>HPLC RT = 7.36 min (method C).<br>LCMS [M + H]$^+$ = 377.1 | Example 2 |
| 15 | 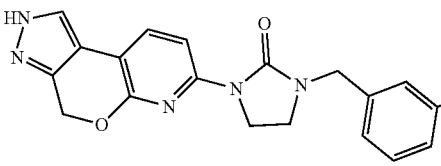<br>1-(2,4-dihydropyrazolo[4',3':4,5]pyrano[2,3-b]pyridin-7-yl)-3-(3-methoxybenzyl)imidazolidin-2-one | $^1$H NMR (400 MHz, DMSO-$d_6$) δ ppm 12.92 (bs, 1 H) 8.09 (s, 1 H) 7.78-7.88 (m, 2 H) 7.25-7.33 (m, 1 H) 6.83-6.91 (m, 3 H) 5.43 (s, 2 H) 4.37 (s, 2 H) 3.84-3.94 (m, 2 H) 3.75 (s, 3 H) 3.09-3.20 (m, 2 H).<br>HPLC RT = 1.58 min (method A).<br>LCMS [M + H]$^+$ = 378.0 | Example 2 |
| 16 | 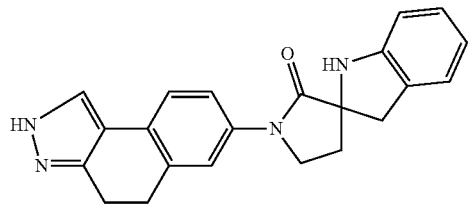 [SMILES: O=C1N(c2ccc3c(c2)CCc2n[nH]cc2-3)CCC12Cc1ccccc1N2]<br>1'-(4,5-dihydro-2H-benzo[e]indazol-7-yl)spiro[indoline-2,3'-pyrrolidin]-2'-one (chiral) | $^1$H NMR (500 MHz, CHLOROFORM-d) δ 7 86 (s, 1H), 7.63 (d, J = 1.9 Hz, 1H), 7.49-7.31 (m, 2H), 7.14-7.02 (m, 2H), 6.90-6.70 (m, 2H), 3.88-3.73 (m, 2H), 3.50-3.38 (m, 1H), 3.21-3.07 (m, 1H), 3.05-2.89 (m, 4H), 2.46-2.26 (m, 2H).<br>HPLC RT = 6.16 min (method C).<br>LCMS [M + H]$^+$ = 357.1. | Example 1 |
| 17 | 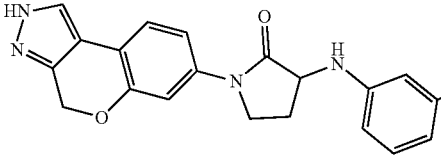<br>1-(2,4-dihydrochromeno[3,4-c]pyrazol-7-yl)-3-((3-methoxyphenyl)amino)pyrrolidin-2-one (Chiral) | $^1$H NMR (400 MHz, METHANOL-$d_4$) δ 7.91 (s, 1H), 7.46 (d, J = 8.4 Hz, 1H), 7.36 (d, J = 2.2 Hz, 1H), 7.31-7.21 (m, 1H), 7.15-7.04 (m, 1H), 6.51-6.35 (m, 2H), 5.27 (s, 2H), 4.42 (dd, J = 10.1, 8.3 Hz, 1H), 3.94-3.83 (m, 2H), 3.79-3.72 (m, 3H), 2.73-2.59 (m, 1H), 2.11-1.92 (m, 1H).<br>HPLC RT = 7.15 min (method C).<br>LCMS [M + H]$^+$ = 377.2. | Example 3 |

TABLE 1-continued

| Example No. | Structure & Name | Analytical Data | Synthetic Method |
|---|---|---|---|
| 18 | 1-(2,4-dihydropyrazolo[4',3':4,5]pyrano[2,3-b]pyridin-7-yl)-3-(3-fluoro-5-methoxybenzyl)imidazolidin-2-one | $^1$H NMR (400 MHz, DMSO-$d_6$) δ ppm 12.92 (br. s., 1 H) 8.06 (s, 1 H) 7.78-7.88 (m, 2 H) 6.67-6.80 (m, 3 H) 5.43 (s, 2 H) 4.37 (s, 2 H) 3.91 (t, J = 8.07 Hz, 2 H) 3.77 (s, 3 H) 3.34-3.40 (m, 2 H). HPLC RT = 1.68 min (method A). LCMS [M + H]$^+$ = 396.1 | Example 2 |
| 19 | 1-(3-methoxybenzyl)-3-(1-methyl-4,5-dihydro-2H-benzo[e]indazol-7-yl)imidazolidin-2-one | $^1$H NMR (400 MHz, METHANOL-$d_4$) δ 7.54-7.34 (m, 3H), 7.32-7.19 (m, 1H), 6.95-6.76 (m, 3H), 4.43 (s, 2H), 3.87 (dd, J = 9.0, 7.3 Hz, 2H), 3.79 (s, 3H), 3.41 (dd, J = 9.1, 7.2 Hz, 2H), 3.02-2.92 (m, 2H), 2.86-2.72 (m, 2H), 2.50 (s, 3H). HPLC RT = 6.08 min (method C). LCMS [M + H]$^+$ = 389.1 | Example 2 |
| 20 | 1-(2,4-dihydropyrazolo[4',3':4,5]pyrano[2,3-b]pyridin-7-yl)-3-(2-fluoro-5-methylbenzyl)imidazolidin-2-one | $^1$H NMR (400 MHz, DMSO-$d_6$) δ ppm 13.24 (bs, 1 H), 8.30-8.36 (m, 1 H), 8.03-8.19 (m, 4 H), 7.75-7.91 (m, 2 H), 5.69 (s, 2 H), 4.75 (s, 2 H), 4.12 (s, 5 H), 3.64 (bs, 2 H). HPLC RT = 1.58 min (method A). LCMS [M + H]$^+$ = 380.2 | Example 2 |
| 21 | 1-(3,5-difluorobenzyl)-3-(2,4-dihydropyrazolo[4',3':4,5]pyrano[2,3-b]pyridin-7-yl)imidazolidin-2-one | $^1$H NMR (400 MHz, DMSO-$d_6$) δ ppm 12.94 (bs, 1H), 8.06 (bs, 1H), 7.83 (q, J = 8.3 Hz, 2H), 7.21-7.11 (m, 1H), 7.05 (dd, J = 8.3, 2.4 Hz, 2H), 5.44 (s, 2H), 4.43 (s, 2H), 3.92 (dd, J = 9.0, 7.1 Hz, 2H), 3.45-3.35 (m, 2H). HPLC RT = 1.49 min (method A). LCMS [M + H]$^+$ = 384.2 | Example 2 |
| 22 | 1-(2,4-dihydropyrazolo[4',3':4,5]pyrano[2,3-b]pyridin-7-yl)-3-(3-fluoro-2-methylbenzyl)imidazolidin-2-one | $^1$H NMR (400 MHz, DMSO-$d_6$) δ ppm 12.93 (bs, 1H), 8.06 (bs, 1H), 7.91-7.70 (m, 2H), 7.30-7.17 (m, 1H), 7 16-7.01 (m, 2H), 5.42 (s, 2H), 4.44 (s, 2H), 3.89 (dd, J = 9.0, 7.1 Hz, 2H), 3.31-3.27 (m, 2H), 2.20 (d, J = 2.0 Hz, 3H). HPLC RT = 1.57 min (method A). LCMS [M + H]$^+$ = 380.2 | Example 2 |

TABLE 1-continued

| Example No. | Structure & Name | Analytical Data | Synthetic Method |
|---|---|---|---|
| 23 | ((3-(2,4-dihydropyrazolo[4',3':4,5]pyrano[2,3-b]pyridin-7-yl)-2-oxoimidazolidin-1-yl)methyl)benzamide | $^1$H NMR (400 MHz, DMSO-$d_6$) δ ppm 12.93 (bs, 1 H), 7.85-7.91 (m, 1 H), 7.77-7.84 (m, 2 H), 7.43-7.50 (m, 2 H), 7.37 (bs, 1 H), 5.43 (s, 2 H), 4.46 (s, 2 H), 3.86-3.96 (m, 2 H), 3.34-3.39 (m, 2 H). HPLC RT = 1.11 min (method A). LCMS [M + H]$^+$ = 391.2 | Example 2 |
| 24 | 1-(2,4-dihydropyrazolo[4',3':4,5]pyrano[2,3-b]pyridin-7-yl)-3-((3-fluoro-2-methylphenyl)amino)pyrrolidin-2-one | $^1$H NMR (400 MHz, DMSO-$d_6$) δ ppm 13.00 (br. s., 1 H) 8.12 (s, 1 H) 7.86-8.02 (m, 2 H) 7.00 (q, J = 7.66 Hz, 1 H) 6.56 (d, J = 8.07 Hz, 1 H) 6.51 (s, 1 H) 6.42 (t, J = 8.93 Hz, 1 H) 5.47 (s, 2 H) 5.37 (d, J = 8.07 Hz, 1 H) 4.53-4.62 (m, 1 H) 4.07 (t, J = 9.17 Hz, 1 H) 3.71-3.81 (m, 1 H) 2.55-2.60 (m, 1 H) 1.96-2.04 (m, 4H). HPLC RT = 1.88 min (method A). LCMS [M + H]$^+$ = 380.1 | Example 3 |
| 25 | 1-(2,4-dihydropyrazolo[4',3':4,5]pyrano[2,3-b]pyridin-7-yl)-3-(3-fluorobenzyl)imidazolidin-2-one | $^1$H NMR (400 MHz, DMSO-$d_6$) δ ppm 12.93 (bs, 1H), 8.06 (s, 1H), 7.88-7.74 (m, 2H), 7.46-7.34 (m, 1H), 7.20-7.06 (m, 3H), 5.43 (s, 2H), 4.42 (s, 2H), 3.94-3.86 (m, 2H), 3.40-3.36 (m, 2H). HPLC RT = 1.40 min (method B). LCMS [M + H]$^+$ = 366.2 | Example 2 |
| 26 | 1-(2,4-dihydropyrazolo[4',3':4,5]pyrano[2,3-b]pyridin-7-yl)-3-(4-fluoro-3-methylbenzyl)imidazolidin-2-one | $^1$H NMR (400 MHz, DMSO-$d_6$) δ ppm 12.93 (bs, 1H), 8.06 (s, 1H), 7.93-7.68 (m, 2H), 7.21 (d, J = 7.3 Hz, 1H), 7.18-7.03 (m, 2H), 5.42 (s, 2H), 4.35 (s, 2H), 3.88 (dd, J = 9.0, 7.1 Hz, 2H), 3.32-3.29 (m, 2H), 2.23 (d, J = 2.0 Hz, 3H). HPLC RT = 1.58 min (method A). LCMS [M + H]$^+$ = 380.2 | Example 2 |
| 27 | 1-(2,4-dihydropyrazolo[4',3':4,5]pyrano[2,3-b]pyridin-7-yl)-3-(2-fluoro-3-methoxybenzyl)imidazolidin-2-one | $^1$H NMR (400 MHz, DMSO-$d_6$) δ ppm 12.92 (bs, 1H), 8.06 (bs, 1H), 7.89-7.72 (m, 2H), 7.20-7.06 (m, 2H), 6.97-6.87 (m, 1H), 5.44 (s, 2H), 4.46 (s, 2H), 3.89 (dd, J = 9.0, 7.0 Hz, 2H), 3.85 (s, 3H), 3.41-3.35 (m, 2H). HPLC RT = 1.38 min (method A). LCMS [M + H]$^+$ = 396.2 | Example 2 |

TABLE 1-continued

| Example No. | Structure & Name | Analytical Data | Synthetic Method |
|---|---|---|---|
| 28 | 1-(2,4-dihydropyrazolo[4',3':4,5]pyrano[2,3-b]pyridin-7-yl)-3-(4-fluoro-2-methylbenzyl)imidazolidin-2-one | $^1$H NMR (400 MHz, DMSO-d$_6$) δ ppm 13.26 (bs, 1 H), 8.27-8.38 (m, 1 H), 8.04-8.16 (m, 2 H), 7.45-7.56 (m, 1 H), 7.33-7.42 (m, 2 H), 5.63-5.76 (m, 2 H), 4.70 (s, 2 H), 4.08-4.21 (m, 2 H), 3.58 (d, J = 8.31 Hz, 2 H), 2.47 (d, J = 1.96 Hz, 3 H) HPLC RT = 1.56 min (method A). LCMS [M + H]$^+$ = 380.2 | Example 2 |
| 29 | 1-(3,4-difluorobenzyl)-3-(2,4-dihydropyrazolo[4',3':4,5]pyrano[2,3-b]pyridin-7-yl)imidazolidin-2-one | $^1$H NMR (400 MHz, DMSO-d$_6$) δ ppm 12.93 (bs, 1H), 8.06 (s, 1H), 7.89-7.74 (m, 2H), 7.48-7.34 (m, 2H), 7.21-7.13 (m, 1H), 5.43 (s, 2H), 4.40 (s, 2H), 3.95-3.84 (m, 2H), 3.39-3.35 (m, 2H). HPLC RT = 1.48 min (method A). LCMS [M + H]$^+$ = 384.2 | Example 2 |
| 30 | 1-(2,5-difluorobenzyl)-3-(2,4-dihydropyrazolo[4',3':4,5]pyrano[2,3-b]pyridin-7-yl)imidazolidin-2-one | $^1$H NMR (400 MHz, DMSO-d$_6$) δ ppm 12.93 (bs, 1H), 8.05 (bs, 1H), 7.89-7.73 (m, 2H), 7.34-7.11 (m, 3H), 5.44 (s, 2H), 4.45 (s, 2H), 3.91 (dd, J = 9.0, 7.1 Hz, 2H), 3.43-3.40 (m, 2H). HPLC RT = 1.45 min (method A). LCMS [M + H]$^+$ = 384.2 | Example 2 |
| 31 | 1-(3-(tert-butyl)benzyl)-3-(2,4-dihydropyrazolo[4',3':4,5]pyrano[2,3-b]pyridin-7-yl)imidazolidin-2-one | HPLC RT = 1.36 min (method A). LCMS [M + H]$^+$ = 406.2 | Example 2 |
| 32 | 3-(benzo[d]thiazol-6-ylamino)-1-(2,4-dihydropyrazolo[4',3':4,5]pyrano[2,3-b]pyridin-7-yl)pyrrolidin-2-one (Racemate) | $^1$H NMR (400 MHz, DMSO-d$_6$) δ ppm 13.00 (bs, 1H), 8.93 (s, 1H), 8.10 (bs, 1H), 7.97 (d, J = 8.0 Hz, 1H), 7.89 (d, J = 8.0 Hz, 1H), 7.78 (d, J = 8.8 Hz, 1H), 7.32 (d, J = 2.3 Hz, 1H), 6.98 (dd, J = 8.9, 2.4 Hz, 1H), 6.33 (d, J = 7.3 Hz, 1H), 5.49 (s, 2H), 4.65-4.47 (m, 1H), 4.09 (t, J = 9.2 Hz, 1H), 3.82-3.75 (m, 1H), 2.61 (d, J = 7.0 Hz, 1H), 1.95-1.87 (m, 1H). HPLC RT = 1.18 min (method A). LCMS [M + H]$^+$ = 405.2 | Example 3 |

TABLE 1-continued

| Example No. | Structure & Name | Analytical Data | Synthetic Method |
|---|---|---|---|
| 33 | 1-(2,6-difluorobenzyl)-3-(2,4-dihydropyrazolo[4',3':4,5]pyrano[2,3-b]pyridin-7-yl)imidazolidin-2-one | $^1$H NMR (400 MHz, DMSO-$d_6$) δ ppm 12.91 (bs, 1H), 8.05 (bs, 1H), 7.89-7.71 (m, 2H), 7.46 (tt, J = 8.4, 6.9 Hz, 1H), 7.25-7.03 (m, 2H), 5.43 (s, 2H), 4.50 (s, 2H), 3.93-3.79 (m, 2H), 3.36 (d, J = 8.0 Hz, 2H).<br>HPLC RT = 1.41 min (method A).<br>LCMS [M + H]$^+$ = 384.2 | Example 2 |
| 34 | 3-((1-(2,4-dihydropyrazolo[4',3':4,5]pyrano[2,3-b]pyridin-7-yl)-2-oxopyrrolidin-3-yl)amino)benzonitrile (Racemate) | $^1$H NMR (400 MHz, DMSO-$d_6$) δ ppm 13.00 (bs, 1H), 8.12 (s, 1H), 7.99-7.82 (m, 2H), 7.32-7.22 (m, 1H), 7.11-7.05 (m, 1H), 7.05-6.99 (m, 1H), 6.97 (dt, J = 7.5, 1.3 Hz, 1H), 6.53 (d, J = 7.5 Hz, 1H), 5.47 (s, 2H), 4.59 (dt, J = 10.2, 8.0 Hz, 1H), 4.07 (t, J = 9.3 Hz, 1H), 3.75 (td, J = 10.3, 7.0 Hz, 1H), 2.62-2.56 (m, 1H), 1.96-1.81 (m, 1H).<br>HPLC RT = 1.37 min (method A).<br>LCMS [M + H]$^+$ = 373.2 | Example 3 |
| 35 | 1-(2,4-dihydropyrazolo[4',3':4,5]pyrano[2,3-b]pyridin-7-yl)-3-((3-(oxazol-5-yl)phenyl)amino)pyrrolidin-2-one (Racemate) | $^1$H NMR (400 MHz, DMSO-$d_6$) δ ppm 13.00 (bs, 1H), 8.39 (s, 1H), 8.11 (bs, 1H), 7.96 (d, J = 8.53 Hz, 1H), 7.89 (d, J = 8.03 Hz, 1H), 7.56 (s, 1H), 7.16-7.23 (m, 1H), 7.06 (t, J = 1.76 Hz, 1H), 6.92-6.99 (m, 1H), 6.73 (dd, J = 8.03, 2.01 Hz, 1H), 6.19 (d, J = 7.53 Hz, 1H), 5.49 (s, 2H), 4.57 (dt, J = 9.91, 7.84 Hz, 1H), 4.03-4.12 (m, 1H), 3.73-3.84 (m, 1H), 2.57-2.63 (m, 1H), 1.84-1.97 (m, 1H).<br>HPLC RT = 1.36 min (method A).<br>LCMS [M + H]$^+$ = 415.2 | Example 3 |

What is claimed is:

1. A compound according to formula (I):

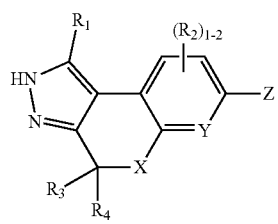

(I)

or a stereoisomer, tautomer, pharmaceutically acceptable salt thereof, wherein

X is independently selected from —$CR_3R_4$—, —O—, and $NR_{5a}$;

Y is independently selected from —$CR_2$ and N;

Z is independently selected from —$NR_5C(O)NR_5(CR_6R_7)_q$—$R_8$, —$NR_5C(O)(CR_6R_7)_q$—$R_8$, —$C(O)NR_5(CR_6R_7)_q$—$R_8$,

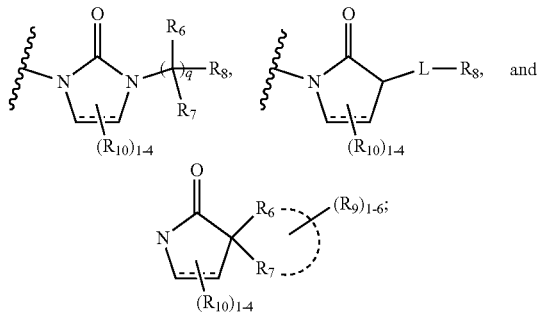

--- is an optional bond;

L is independently selected from —$(CR_6R_7)_q$—, —$NR_{5a}(CR_6R_7)_q$—, and —$O(CR_6R_7)_q$—;

$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, —$(CH_2)_rOR_b$;

$R_3$ and $R_4$ are independently selected from H and $C_{1-4}$ alkyl substituted with 0-3 $R_e$;

$R_5$ is independently selected from H and $C_{1-4}$ alkyl;

$R_{5a}$ is independently selected from H and $C_{1-4}$ alkyl;

R₆ and R₇ are independently selected from H, C₁₋₄alkyl substituted with 0-4 R_e, —(CH₂)_rOR_b, —(CH₂)_rS(O)_pR_c, —(CH₂)_rC(=O)R_b, —(CH₂)_rNR_aR_a, —(CH₂)_rC(=O)(CH₂)_rNR_aR_a, —(CH₂)_rNR_aC(=O)R_b, —(CH₂)_r NR_aC(=O)OR_b, —(CH₂)_rOC(=O)NR_aR_a, —(CH₂)_rNR_aC(=O)NR_aR_a, —(CH₂)_rC(=O)OR_b, —(CH₂)_rS(O)_pNR_aR_a, —(CH₂)_rNR_aS(O)_pNR_aR_a, —(CH₂)_rNR_aS(O)_pR_c, (CH₂)_r—C₃₋₆ carbocyclyl substituted with 0-3 R_e, and —(CH₂)_r-heterocyclyl substituted with 0-3 R_e;

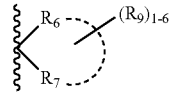

is independently selected from carbocyclyl and heterocyclyl;

R₈ is selected from C₃₋₁₀carbocyclyl and heterocyclyl, each substituted with 1-5 R₉;

R₉ is independently selected from H, F, Cl, Br, C₁₋₄alkyl substituted with 0-5 R_e, C₂₋₄alkenyl substituted with 0-5 R_e, C₂₋₄alkynyl substituted with 0-5 R_e, =O, nitro, —(CHR_d)_rS(O)_pR_c, —(CHR_d)_rS(O)_pNR_aR_a, —(CHR_d)_rNR_aS(O)_pR_c, —(CHR_d)_rOR_b, —(CHR_d)_rCN, —(CHR_d)_rNR_aR_a, —(CHR_d)_rNR_aC(=O)R_b, —(CHR_d)_rNR_aC(=O)NR_aR_a, —(CHR_d)_rC(=O)OR_b, —(CHR_d)_rC(=O)R_b, —(CHR_d)_r OC(=O)R_b, —(CHR_d)_rC(=O)NR_aR_a, —(CHR_d)_r-cycloalkyl, —(CHR_d)_r-heterocyclyl, —(CHR_d)_r-aryl, and —(CHR_d)_r-heteroaryl, wherein said alkyl, cycloalkyl, heterocyclyl, aryl, or heteroaryl is substituted with 0-4 R_e;

alternatively, two adjacent R₉ groups are combined to form a carbocyclic or heterocyclic ring comprising carbon atoms and 1-3 hetero atoms selected from N, O, and S(O)_p, wherein the carbocyclic and heterocyclic rings are substituted with 0-4 R_e;

R₁₀ is independently selected from H, =O, C₁₋₄alkyl substituted with 0-4 R_e, —(CH₂)_rOR_b, C(=O)R_b, and —C(=O)OR_b;

R_a, at each occurrence, is independently selected from H, C₁₋₆ alkyl substituted with 0-5 R_e, C₂₋₆alkenyl substituted with 0-5 R_e, C₂₋₆alkynyl substituted with 0-5 R_e, —(CH₂)_r—C₃₋₁₀carbocyclyl substituted with 0-5 R_e, and —(CH₂)_r-heterocyclyl substituted with 0-5 R_e; or R_a and R_a together with the nitrogen atom to which they are both attached form a heterocyclic ring substituted with 0-5 R_e;

R_b, at each occurrence, is independently selected from H, C₁₋₆ alkyl substituted with 0-5 R_e, C₂₋₆ alkenyl substituted with 0-5 R_e, C₂₋₆ alkynyl substituted with 0-5 R_e, —(CH₂)_r—C₃₋₁₀carbocyclyl substituted with 0-5 R_e, and —(CH₂)_r-heterocyclyl substituted with 0-5 R_e;

R_c, at each occurrence, is independently selected from C₁₋₆ alkyl substituted with 0-5 R_e, C₂₋₆alkenyl substituted with 0-5 R_e, C₂₋₆alkynyl substituted with 0-5 R_e, C₃₋₆carbocyclyl, and heterocyclyl;

R_d, at each occurrence, is independently selected from H and C₁₋₄alkyl substituted with 0-5 R_e;

R_e, at each occurrence, is independently selected from C₁₋₆ alkyl (optionally substituted with F, Cl, and Br, OH), C₂₋₆ alkenyl, C₂₋₆ alkynyl, —(CH₂)_r—C₃₋₁₀ carbocyclyl, —(CH₂)_r-heterocyclyl, F, Cl, Br, CN, NO₂, =O, CO₂H, CO₂C₁₋₆ alkyl, —(CH₂)_rOC₁₋₅ alkyl, —(CH₂)_rOH, —(CH₂)_rNR_fR_f, —(CH₂)_rNR_fR_fC(=O)C₁₋₄alkyl, —C(=O)NR_fR_f, —C(=O)R_f, S(O)_pNR_fR_f, —NR_fR_fS(O)_pC₁₋₄alkyl, and S(O)_pC₁₋₄alkyl;

R_f, at each occurrence, is independently selected from H, F, Cl, Br, C₁₋₅alkyl, C₃₋₆ cycloalkyl; or R_f and R_f together with the nitrogen atom to which they are both attached form a heterocyclic ring;

p, at each occurrence, is independently selected from zero, 1, and 2;

q, at each occurrence, is independently selected from zero, 1, 2, and 3; and r, at each occurrence, is independently selected from zero, 1, 2, 3, and 4.

2. The compound of claim 1, having Formula (II):

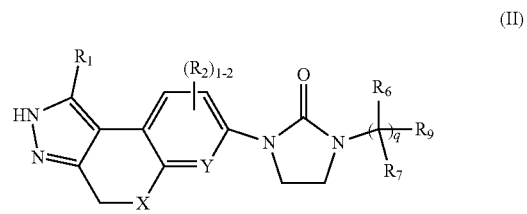

(II)

or a stereoisomer, tautomer, pharmaceutically acceptable salt thereof, wherein

X is independently selected from —CH₂—, and —O—;

Y is independently selected from —CR₂ and N;

R₁ is independently selected from H, F, Cl, Br, CN, NR_aR_a, —OC₁₋₄ alkyl substituted with 0-3 R_e, C₁₋₄ alkyl substituted with 0-3 R_e, and —(CH₂)_rOR_b;

R₂ is independently selected from H, F, Cl, Br, CN, NR_aR_a, —OC₁₋₄ alkyl substituted with 0-3 R_e, C₁₋₄ alkyl substituted with 0-3 R_e, and —(CH₂)_rOR_b;

R₆ and R₇ are independently selected from H and C₁₋₄alkyl substituted with 0-4 R_e;

R₈ is selected from phenyl, C₃₋₆ cycloalkyl and heterocyclyl, each substituted with 1-5 R₉;

R₉ is independently selected from H, F, Cl, C₁₋₄alkyl substituted with 0-5 R_e, —C(=O)NR_aR_a—NR_aS(O)_pC₁₋₄ alkyl, —OR_b, and —CN;

R_a, at each occurrence, is independently selected from H, C₁₋₆ alkyl substituted with 0-5 R_e, —(CH₂)_r—C₃₋₁₀carbocyclyl substituted with 0-5 R_e, and —(CH₂)_r-heterocyclyl substituted with 0-5 R_e;

R_b, at each occurrence, is independently selected from H and C₁₋₆ alkyl substituted with 0-5 R_e;

R_e, at each occurrence, is independently selected from C₁₋₆ alkyl (optionally substituted with F, Cl, and Br, OH), F, Cl, Br, CN, NO₂, —(CH₂)_rOC₁₋₅ alkyl, —(CH₂)_rOH;

p, at each occurrence, is independently selected from zero, 1, and 2;

q, at each occurrence, is independently selected from zero, 1, 2, and 3; and r, at each occurrence, is independently selected from zero, 1, 2, 3, and 4.

3. The compound of claim 2, having Formula (III):

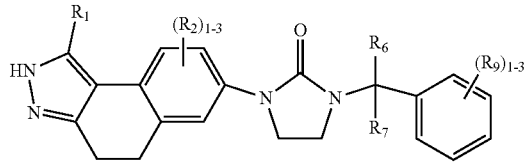

(III)

or a stereoisomer, tautomer, pharmaceutically acceptable salt thereof, wherein
$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_6$ and $R_7$ are independently selected from H and Me;
$R_9$ is independently selected from H, F, Cl, $C_{1-4}$alkyl substituted with 0-5 $R_e$, and —$OC_{1-4}$alkyl;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;
$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and
r, at each occurrence, is independently selected from zero, 1, 2, 3, and 4.

4. The compound of claim 2, having Formula (IV):

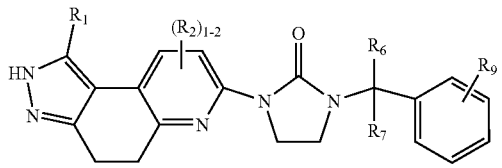

(IV)

or a stereoisomer, tautomer, pharmaceutically acceptable salt thereof, wherein
$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_6$ and $R_7$ are independently selected from H and Me;
$R_9$ is independently selected from H, F, Cl, $C_{1-4}$alkyl substituted with 0-5 $R_e$, and —$OC_{1-4}$alkyl;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;
$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and
r, at each occurrence, is independently selected from zero, 1, 2, 3, and 4.

5. The compound of claim 2, having Formula (V):

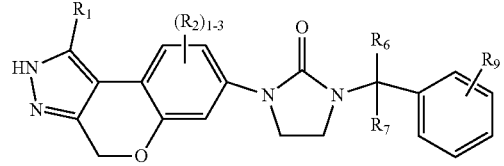

(V)

or a stereoisomer, tautomer, pharmaceutically acceptable salt thereof, wherein
$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_6$ and $R_7$ are independently selected from H and Me;
$R_9$ is independently selected from H, F, Cl, $C_{1-4}$alkyl substituted with 0-5 $R_e$, and —$OC_{1-4}$alkyl;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;
$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and
r, at each occurrence, is independently selected from zero, 1, 2, 3, and 4.

6. The compound of claim 2, having Formula (VI):

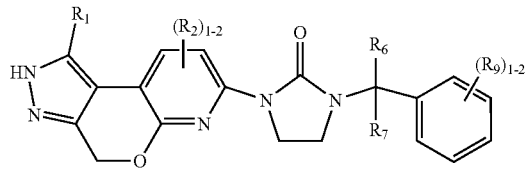

(VI)

or a stereoisomer, tautomer, pharmaceutically acceptable salt thereof, wherein
$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_6$ and $R_7$ are independently selected from H and Me;
$R_9$ is independently selected from H, F, Cl, $C_{1-4}$alkyl substituted with 0-5 $R_e$, and —$OC_{1-4}$alkyl;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and r, at each occurrence, is independently selected from zero, 1, 2, 3, and 4.

7. The compound of claim 1, having Formula (VII):

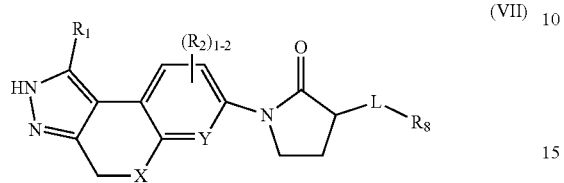

(VII)

or a stereoisomer, tautomer, pharmaceutically acceptable salt thereof, wherein

X is independently selected from —$CH_2$—, and —O—;
Y is independently selected from —$CR_2$ and N;
L is independently selected from —$CR_6R_7$, —$NR_{5a}$—, and —O—;
$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_6$ and $R_7$ are independently selected from H and $C_{1-4}$alkyl substituted;
$R_8$ is selected from phenyl, $C_{3-6}$ cycloalkyl and heterocyclyl, each substituted with 1-5 $R_9$;
$R_9$ is independently selected from H, F, Cl, $C_{1-4}$alkyl substituted with 0-5 $R_e$, —$OR_b$, and heteroaryl;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;
$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$;
p, at each occurrence, is independently selected from zero, 1, and 2; and
r, at each occurrence, is independently selected from zero, 1, 2, 3, and 4.

8. The compound of claim 7, having Formula (VIII):

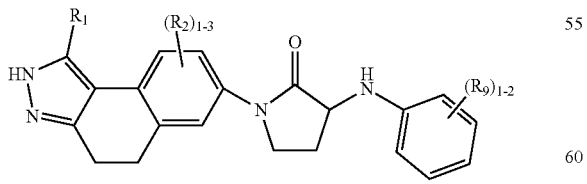

(VIII)

or a stereoisomer, tautomer, pharmaceutically acceptable salt thereof, wherein $R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_9$ is independently selected from H, F, Cl, CN, $C_{1-4}$alkyl substituted with 0-5 $R_e$, and —$OC_{1-4}$alkyl;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;
$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and
r, at each occurrence, is independently selected from zero, 1, 2, 3, and 4.

9. The compound of claim 7, having Formula (IX):

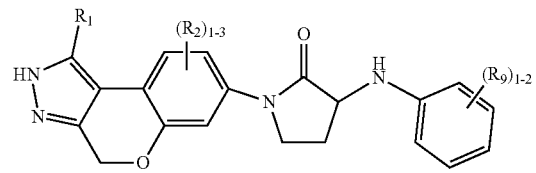

(IX)

or a stereoisomer, tautomer, pharmaceutically acceptable salt thereof, wherein $R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_9$ is independently selected from H, F, Cl, CN, $C_{1-4}$alkyl substituted with 0-5 $R_e$, and —$OC_{1-4}$alkyl;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;
$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and
r, at each occurrence, is independently selected from zero, 1, 2, 3, and 4.

10. The compound of claim 7, having Formula (X):

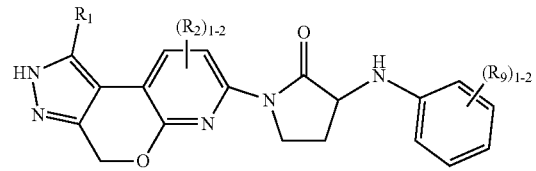

(X)

or a stereoisomer, tautomer, pharmaceutically acceptable salt thereof, wherein $R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;

$R_9$ is independently selected from H, F, Cl, CN, $C_{1-4}$alkyl substituted with 0-5 $R_e$, and —$OC_{1-4}$alkyl;

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$; and r, at each occurrence, is independently selected from zero, 1, 2, 3, and 4.

11. The compound of claim 1, having Formula (XI):

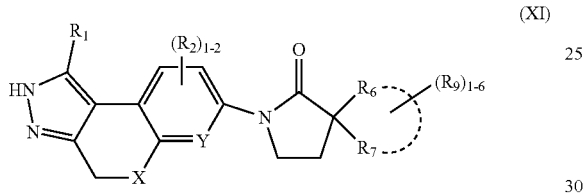

(XI)

or a stereoisomer, tautomer, pharmaceutically acceptable salt thereof, wherein

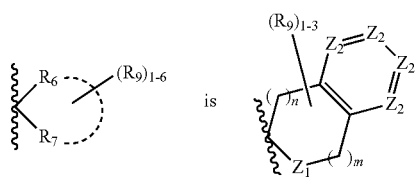

X is independently selected from —$CH_2$—, and —O—;
Y is independently selected from —$CR_2$ and N;
$Z_1$ is independently selected from $CR_9R_9$, O, NH, and $NC_{1-4}$alkyl;
$Z_2$ is independently selected from $CR_9$ and N; provided no more than three of $Z_2$ are N;
$R_1$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_2$ is independently selected from H, F, Cl, Br, CN, $NR_aR_a$, —$OC_{1-4}$ alkyl substituted with 0-3 $R_e$, $C_{1-4}$ alkyl substituted with 0-3 $R_e$, and —$(CH_2)_rOR_b$;
$R_9$ is independently selected from H, F, Cl, and $C_{1-4}$alkyl substituted with 0-5 $R_e$;
$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_b$, at each occurrence, is independently selected from H and $C_{1-6}$ alkyl substituted with 0-5 $R_e$;
$R_e$, at each occurrence, is independently selected from $C_{1-6}$ alkyl (optionally substituted with F, Cl, and Br, OH), F, Cl, Br, CN, $NO_2$, —$(CH_2)_rOC_{1-5}$ alkyl, —$(CH_2)_rOH$;

m is independently selected from 0 and 1;
n is independently selected from 1 and 2; and
r, at each occurrence, is independently selected from zero, 1, 2, 3, and 4.

12. The compound of claim 11, having Formula (XII):

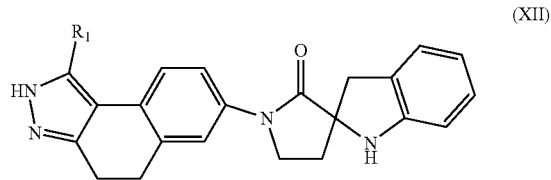

(XII)

or a stereoisomer, tautomer, pharmaceutically acceptable salt thereof, wherein $R_1$ is independently selected from H and $C_{1-4}$ alkyl.

13. The compound of claim 1, having Formula (XIII):

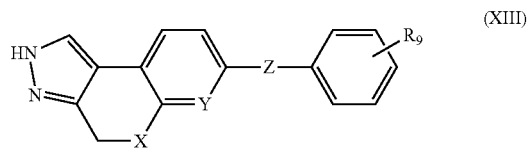

(XIII)

or a stereoisomer, tautomer, pharmaceutically acceptable salt thereof, wherein

X is independently selected from —$CH_2$—, and —O—;
Y is independently selected from —$CR_2$ and N;
Z is independently selected from —$NR_5C(O)NR_5(CR_6R_7)_q$—, —$NR_5C(O)CR_6R_7$-L-, and —$C(O)NR_5(CR_6R_7)_q$—;
L is independently selected from —$(CR_6R_7)_q$—, and —$NR_{5a}(CR_6R_7)_q$—;
$R_6$ and $R_7$ are independently selected from H, $C_{1-4}$alkyl, and $NH_2$;
$R_9$ is independently selected from H, F, Cl, $C_{1-4}$alkyl, and —$OC_{1-4}$alkyl; and
q, at each occurrence, is independently selected from zero, 1, and 2.

14. A pharmaceutical composition comprising one or more compounds according to claim 1 and a pharmaceutically acceptable carrier or diluent.

15. The compound of claim 1, selected from the group consisting of

1'-(4,5-dihydro-2H-benzo[e]indazol-7-yl)spiro[indoline-2,3'-pyrrolidin]-2'-one, 1-(4,5-dihydro-2H-benzo[e]indazol-7-yl)-3-(3-methoxybenzyl)imidazolidin-2-one, (S)-1-(4,5-dihydro-2H-benzo[e]indazol-7-yl)-3-((3-methoxyphenyl)amino)pyrrolidin-2-one, (R)-2-amino-N-(4,5-dihydro-2H-benzo[e]indazol-7-yl)-4-phenylbutanamide, 1-(2,4-dihydropyrazolo[4',3':4,5]pyrano[2,3-b]pyridin-7-yl)-3-(3-methoxybenzyl)urea, 1'-(4,5-dihydro-2H-benzo[e]indazol-7-yl)spiro[indoline-2,3'-pyrrolidin]-2'-one, (R)-1-(4,5-dihydro-2H-benzo[e]indazol-7-yl)-3-(1-(3-methoxyphenyl)ethyl)imidazolidin-2-one, 1-(4,5-dihydro-2H-pyrazolo[4,3-f]quinolin-7-yl)-3-(3-methoxybenzyl)imidazolidin-2-one, (R)-1-(4,5-dihydro-2H-benzo[e]indazol-7-yl)-3-((3-methoxyphenyl)amino)pyrrolidin-2-one, 1-(2,4-dihydrochromeno[3,4-c]pyrazol-7-yl)-3-((3-methoxyphenyl)amino)pyrrolidin-2-one,
1-(2,4-dihydropyrazolo[4',3':4,5]pyrano[2,3-b]pyridin-7-yl)-3-((3-methoxyphenyl)amino)pyrrolidin-2-one,
1-(2,4-dihydropyrazolo[4',3':4,5]pyrano[2,3-b]pyridin-7-yl)-3-((3-fluoro-5-methoxyphenyl)amino)pyrrolidin-2-one,
1-(2,4-dihydrochromeno[3,4-c]pyrazol-7-yl)-3-((3-methoxyphenyl)amino)pyrrolidin-2-one,
1-(2,4-dihydrochromeno[3,4-c]pyrazol-7-yl)-3-(3-methoxybenzyl)imidazolidin-2-one,
1-(2,4-dihydropyrazolo[4',3':4,5]pyrano[2,3-b]pyridin-7-yl)-3-(3-methoxybenzyl)imidazolidin-2-one,
1'-(4,5-dihydro-2H-benzo[e]indazol-7-yl)spiro[indoline-2,3'-pyrrolidin]-2'-one,
1-(2,4-dihydrochromeno[3,4-c]pyrazol-7-yl)-3-((3-methoxyphenyl)amino)pyrrolidin-2-one,
1-(2,4-dihydropyrazolo[4',3':4,5]pyrano[2,3-b]pyridin-7-yl)-3-(3-fluoro-5-methoxybenzyl)imidazolidin-2-one,
1-(3-methoxybenzyl)-3-(1-methyl-4,5-dihydro-2H-benzo[e]indazol-7-yl)imidazolidin-2-one,
1-(2,4-dihydropyrazolo[4',3':4,5]pyrano[2,3-b]pyridin-7-yl)-3-(2-fluoro-5-methylbenzyl)imidazolidin-2-one,
1-(3,5-difluorobenzyl)-3-(2,4-dihydropyrazolo[4',3':4,5]pyrano[2,3-b]pyridin-7-yl)imidazolidin-2-one,
1-(2,4-dihydropyrazolo[4',3':4,5]pyrano[2,3-b]pyridin-7-yl)-3-(3-fluoro-2-methylbenzyl)imidazolidin-2-one,
3-((3-(2,4-dihydropyrazolo[4',3':4,5]pyrano[2,3-b]pyridin-7-yl)-2-oxoimidazolidin-1-yl)methyl)benzamide,
1-(2,4-dihydropyrazolo[4',3':4,5]pyrano[2,3-b]pyridin-7-yl)-3-((3-fluoro-2-methylphenyl)amino)pyrrolidin-2-one,
1-(2,4-dihydropyrazolo[4',3':4,5]pyrano[2,3-b]pyridin-7-yl)-3-(3-fluorobenzyl)imidazolidin-2-one,
1-(2,4-dihydropyrazolo[4',3':4,5]pyrano[2,3-b]pyridin-7-yl)-3-(4-fluoro-3-methylbenzyl)imidazolidin-2-one,
1-(2,4-dihydropyrazolo[4',3':4,5]pyrano[2,3-b]pyridin-7-yl)-3-(2-fluoro-3-methoxybenzyl)imidazolidin-2-one,
1-(2,4-dihydropyrazolo[4',3':4,5]pyrano[2,3-b]pyridin-7-yl)-3-(4-fluoro-2-methylbenzyl)imidazolidin-2-one,
1-(3,4-difluorobenzyl)-3-(2,4-dihydropyrazolo[4',3':4,5]pyrano[2,3-b]pyridin-7-yl)imidazolidin-2-one,
1-(2,5-difluorobenzyl)-3-(2,4-dihydropyrazolo[4',3':4,5]pyrano[2,3-b]pyridin-7-yl)imidazolidin-2-one,
1-(3-(tert-butyl)benzyl)-3-(2,4-dihydropyrazolo[4',3':4,5]pyrano[2,3-b]pyridin-7-yl)imidazolidin-2-one,
3-(benzo[d]thiazol-6-ylamino)-1-(2,4-dihydropyrazolo[4',3':4,5]pyrano[2,3-b]pyridin-7-yl)pyrrolidin-2-one,
1-(2,6-difluorobenzyl)-3-(2,4-dihydropyrazolo[4',3':4,5]pyrano[2,3-b]pyridin-7-yl)imidazolidin-2-one,
3((1-(2,4-dihydropyrazolo[4',3':4,5]pyrano[2,3-b]pyridin-7-yl)-2-oxopyrrolidin-3-yl)amino)benzonitrile, and
1-(2,4-dihydropyrazolo[4',3':4,5]pyrano[2,3-b]pyridin-7-yl)-3-((3-(oxazol-5-yl)phenyl)amino)pyrrolidin-2-one.

* * * * *